(12) United States Patent
Wei

(10) Patent No.: US 10,603,444 B2
(45) Date of Patent: Mar. 31, 2020

(54) AUTOMATIC INJECTION DEVICE WITH VARIABLE DOSING

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 457 days.

(21) Appl. No.: 15/503,389

(22) PCT Filed: Aug. 28, 2015

(86) PCT No.: PCT/US2015/047477
§ 371 (c)(1),
(2) Date: Feb. 11, 2017

(87) PCT Pub. No.: WO2016/036600
PCT Pub. Date: Mar. 10, 2016

(65) Prior Publication Data
US 2017/0239424 A1 Aug. 24, 2017

Related U.S. Application Data

(60) Provisional application No. 62/046,191, filed on Sep. 5, 2014, provisional application No. 62/155,509, filed on May 1, 2015.

(51) Int. Cl.
*A61M 5/315* (2006.01)
*A61M 5/32* (2006.01)
*A61M 5/20* (2006.01)

(52) U.S. Cl.
CPC ...... *A61M 5/31593* (2013.01); *A61M 5/3155* (2013.01); *A61M 5/3158* (2013.01);
(Continued)

(58) Field of Classification Search
CPC .......... A61M 5/31593; A61M 5/31538; A61M 5/31563; A61M 5/31571; A61M 5/3158;
(Continued)

(56) References Cited

U.S. PATENT DOCUMENTS 5,391,151 A * 2/1995 Wilmot ............... A61M 5/2033
604/135
5,480,387 A * 1/1996 Gabriel .................. A61M 5/20
604/134
(Continued)

*Primary Examiner* — Matthew F Desanto
(74) *Attorney, Agent, or Firm* — Min Wei

(57) ABSTRACT

A medication delivery device, for use with a container having a distal end and a needle being placed at the distal end of the container, including: a push rod which is movable with respect to at least a portion of the container; a resilient member configured to bias the push rod to move toward the distal end of the container; a releasable restraining means configured to releasably restrain the push rod in a locked state against the biasing of the resilient member; a means to adjust amount of movement of the push rod with respect to the container in order to deliver a predetermined dose of medication; and an activation means configured to release the releasable means. The means to adjust amount of movement of the push rod with respect to the container is bi-directional. The device can accommodate containers of different size or shape.

11 Claims, 31 Drawing Sheets

(52) U.S. Cl.
CPC .... *A61M 5/31538* (2013.01); *A61M 5/31563* (2013.01); *A61M 5/31571* (2013.01); *A61M 5/3202* (2013.01); *A61M 5/3204* (2013.01); *A61M 2005/206* (2013.01); *A61M 2005/2026* (2013.01)

(58) Field of Classification Search
CPC .............. A61M 5/3202; A61M 5/3204; A61M 2005/2026; A61M 2005/206
See application file for complete search history.

(56) References Cited

U.S. PATENT DOCUMENTS

| | | | | |
|---|---|---|---|---|
| 5,514,097 | A | * | 5/1996 | Knauer ................... A61M 5/20 604/136 |
| 9,308,327 | B2 | * | 4/2016 | Marshall ............. A61M 5/2033 |
| 2011/0301548 | A1 | * | 12/2011 | Young ................ A61M 5/2033 604/200 |

* cited by examiner

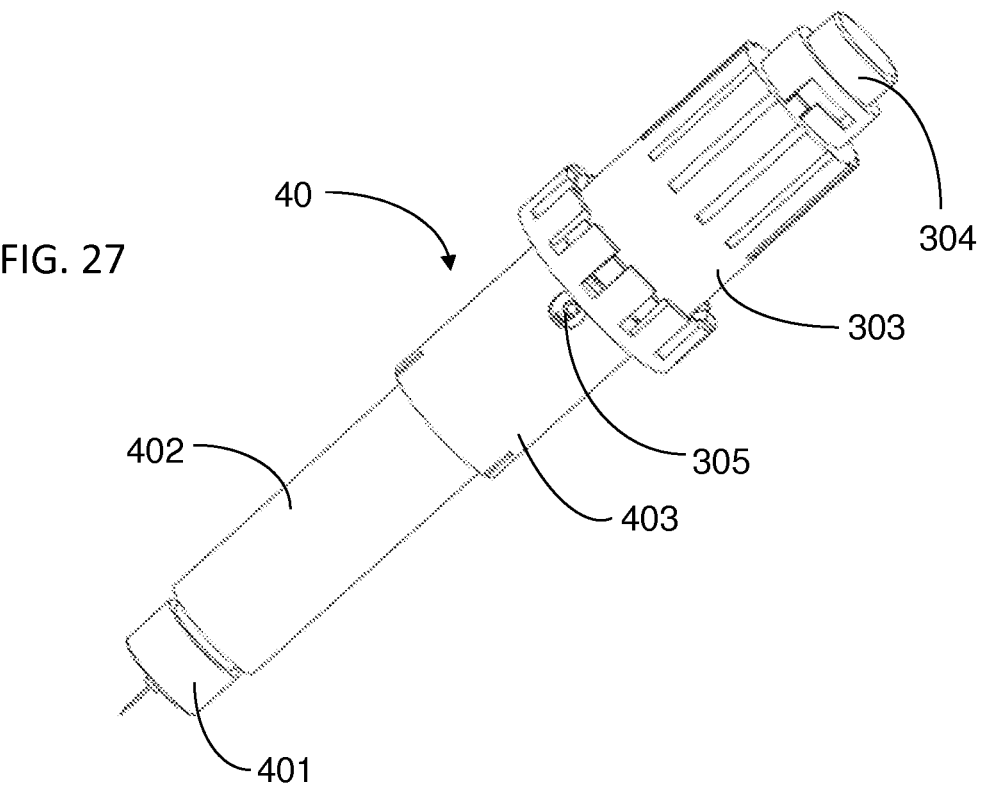
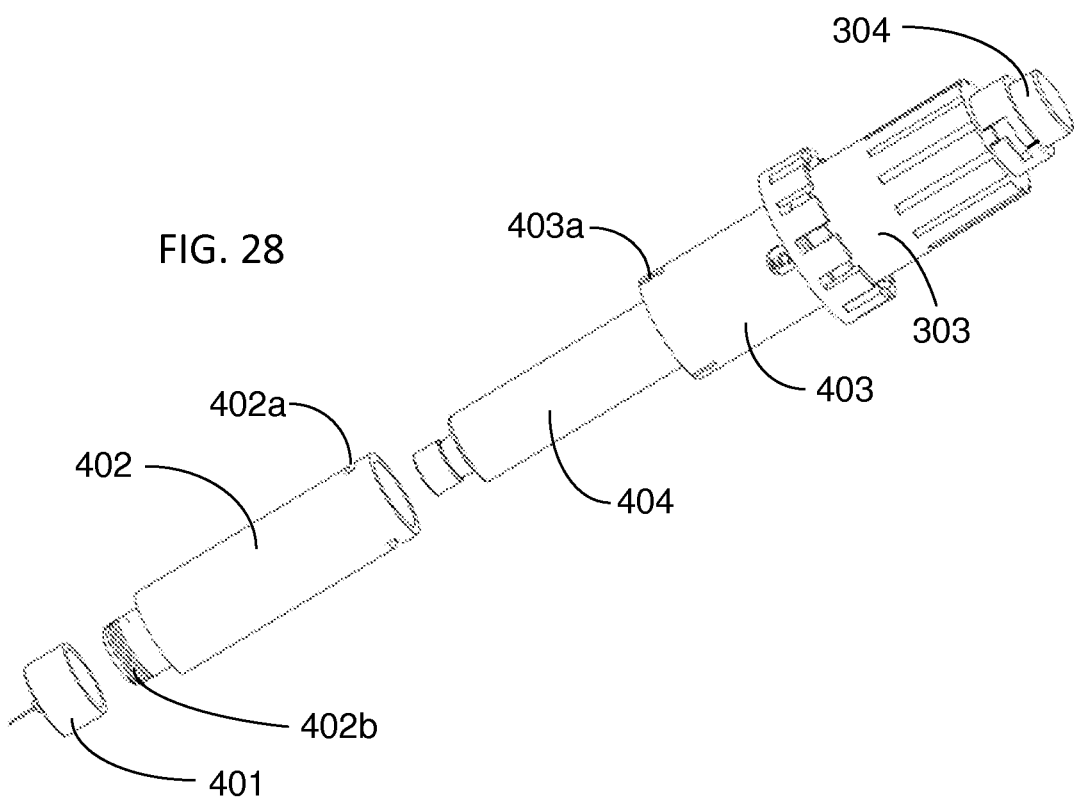

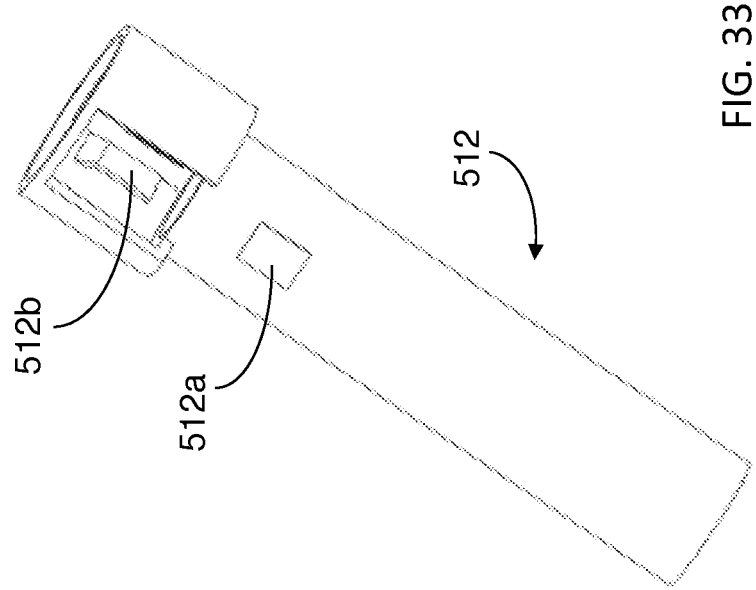
FIG. 33
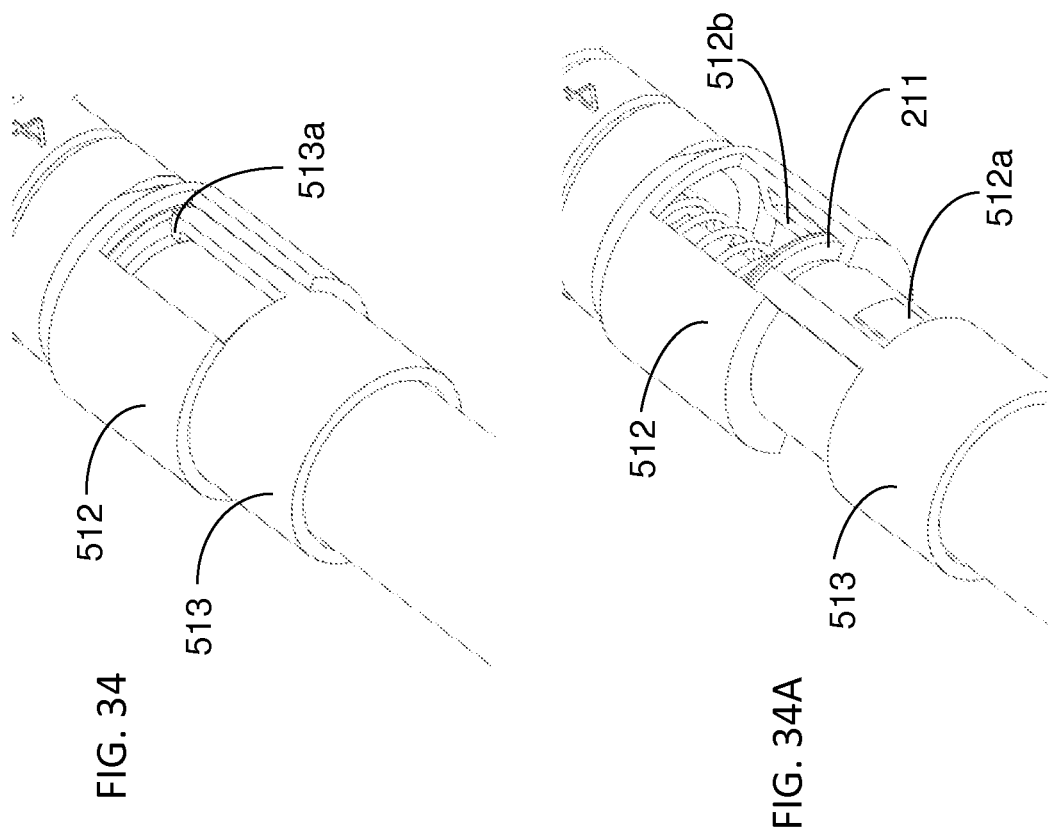
FIG. 34
FIG. 34A

AUTOMATIC INJECTION DEVICE WITH VARIABLE DOSING

TECHNICAL FIELD

The invention relates to an automatic medication delivery device for delivering liquid medications.

BACKGROUND OF THE INVENTION

As biologic drugs increase in popularity, parenteral delivery devices are expected to be widely used. Injection drug delivery devices, such like the automatic injection devices, can ease medication preparation/administration and reduce needle injury, which results in improved patient convenience and compliance. Due to the advantages mentioned above, more patients and healthcare professionals prefer automatic injection devices to the traditional manual syringes. However, current automatic injection devices are mostly designed for fix dose delivery. This limits the use of parenteral drugs that require variable dosing for different patient population as well as different therapeutic treatments. Although there are injection devices, such as insulin pen, can be used to inject variable doses, those devices often don't have automatic injection function and/or cannot be used to inject relatively large volume, for example, more than 0.5 mL for a single injection. Moreover, the dose setting for insulin pen type of injector is often unidirectional, which is very inconvenient for users. As an example, the "Instructions for Use" of insulin injection device Autopen® developed by Owen Mumford Ltd requires users not to dial back dose. If at any time the dose has been over dialed using the Autopen® device, it is recommended that the incorrect dose is fully expelled into air and the required dose is redialed. Meantime, while US patent application US 2010/0010454 discloses an automatic injection device for delivering variable dose, the disclosed device in US patent application US 2010/0010454 doesn't disclose a mechanism to prevent the radial rotation and back-threading of the push rod (named as plunger in the US patent application US 2010/0010454) after the injection device is activated. Consequently, the target delivery dose cannot be achieved by using the device embodiment disclosed in US patent application US 2010/0010454. Therefore, injection devices based on a novel design principal are in need.

SUMMARY OF THE INVENTION

It is an object of the present invention to provide an automatic medication delivery device. This invention is to overcome one or more of the disadvantages of the prior art.

It is an advantage of the present invention that the automatic medication delivery device embodiments here can be used for delivering variable dose and provide option for users to adjust injection dose up to entire content of the medication container in the device embodiments.

It is an advantage of the present invention that the automatic medication delivery device embodiments here have automatic injection function, assisted by mechanical spring, so that the injection device embodiments are ergonomic to use for delivering high volume, highly viscous medications.

It is an advantage of the present invention that the injection volume can be pre-determined and the pre-determined injection volume will not change during the entire injection process.

It is an advantage of the present invention that, in at least one embodiment, the dose setting is bidirectional. By using the embodiments in the present invention, user can simply either increase dose or decrease dose by moving the dose setting mechanism in either direction, in the same manner, until the correct dose is selected, before injection.

It is an advantage of the present invention that, in at least one embodiment, the automatic medication delivery device works with pre-filled medication container.

It is an advantage of the present invention that, in at least one embodiment, the maximum automatic dose can be set by a medical professional or patient to prevent over dose.

It is an advantage of the present invention that, in at least one embodiment, the injection dose can be pre-set by a pharmacist or medical professional, and patient will not be able to change the pre-set dose thereafter.

It is a further advantage of the present invention that, in at least one embodiment, the dose setting mechanism can be customized for different medications and/or different patients.

Due to the simplicity of its operation and its unique functional features, the medication delivery device embodiments of this invention are well suited for use by a wide range of patients including children and those with permanent or temporary disabilities.

BRIEF DESCRIPTION OF THE DRAWINGS

The figures are schematic and simplified for clarity, and they just show details, which are essential to the understanding of the invention, while other details are left out. Throughout, the same reference numerals are used for identical or corresponding parts.

FIG. 27 is a perspective view of the third alternative automatic medication delivery device assembly according to the invention.

FIG. 28 is an exploded view of the third alternative automatic medication delivery device assembly according to the invention.

FIG. 33 is a perspective view of a component used in the fourth alternative automatic medication delivery device assembly according to the invention.

FIGS. 34 and 34A show engagements between components of the fourth alternative automatic medication delivery device assembly according to the invention.

FIG. 37-37C show steps of using the fifth alternative automatic medication delivery device assembly according to the invention.

FIG. 53-53B show steps of using the ninth alternative automatic medication delivery device assembly according to the invention.

Corresponding parts are marked with the same reference symbols in all figures.

DETAILED DESCRIPTION THE DRAWINGS

Figure 1:
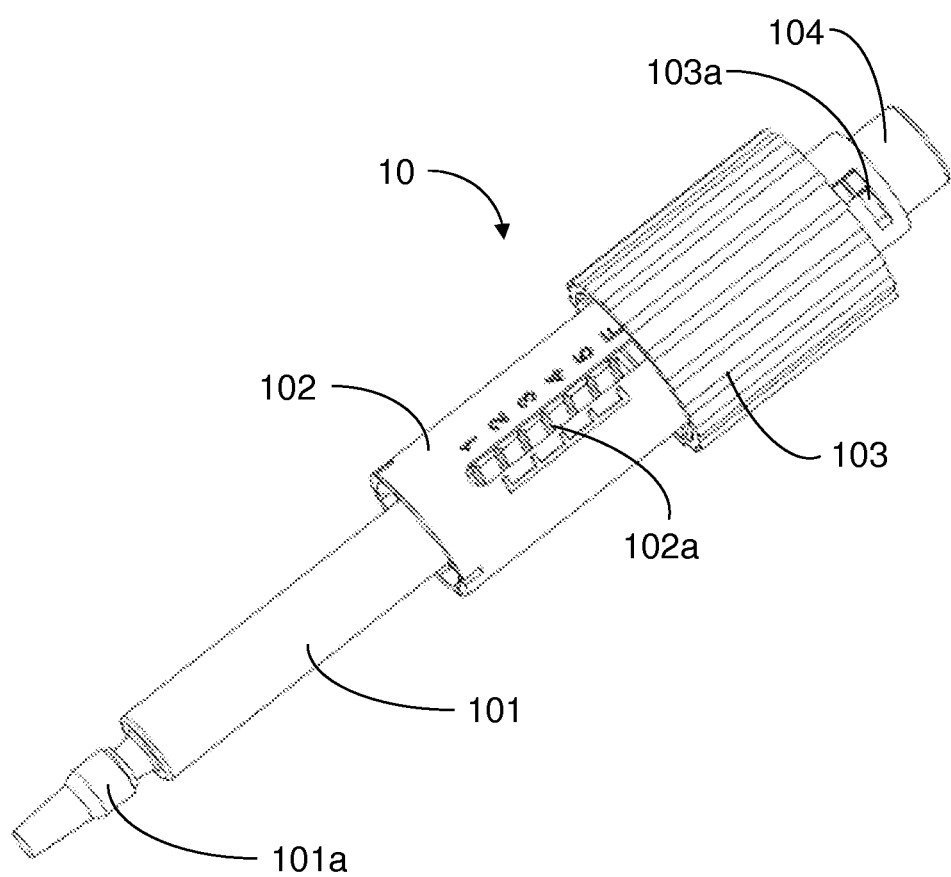
FIG. 1 is a perspective view of an exemplary automatic medication delivery device assembly according to the invention.

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as a drug, into a patient. Initially it may be convenient to define that, the term "distal end" is meant to refer to the end of the automatic medication delivery device assembly inserted into the patient, whereas the term "proximal end" is meant to refer to the end opposite to the "distal end" along the longitudinal axis of the device body. The words "upper", "lower", "right" and "left" designate directions in the drawings to which reference is made. The Words "inward" and "outward" refer to directions toward and away from, respectively, FIGS. 1-7 illustrate the construction and function mechanism of an exemplary automatic medication delivery device assembly 10 according to the invention.

Figure 2:
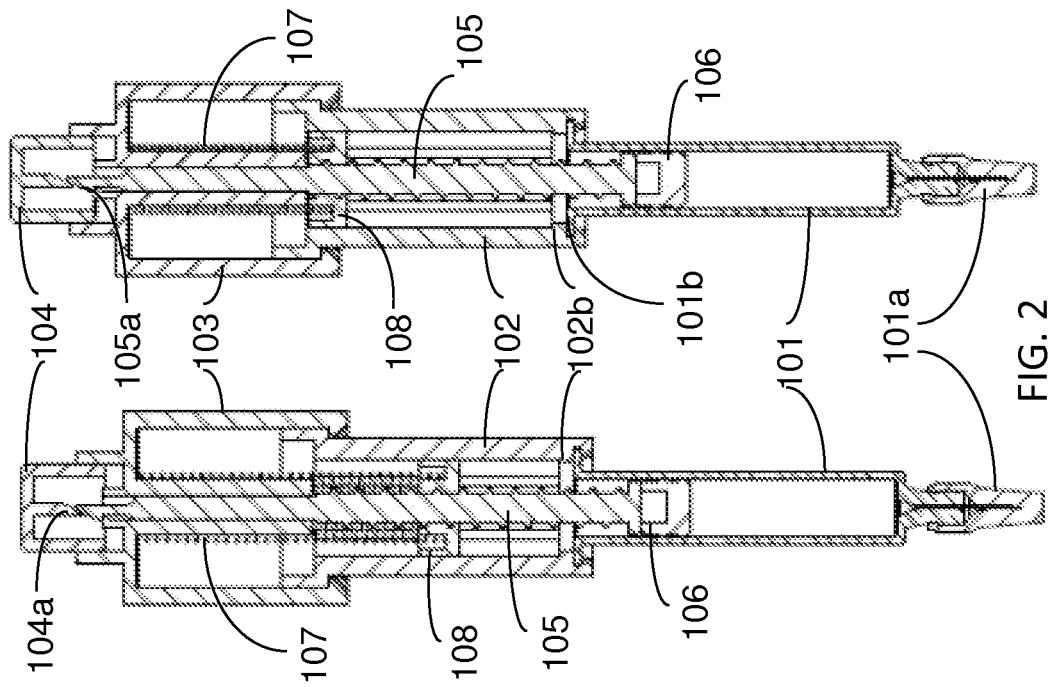
FIG. 2 shows cross-sectional views of the exemplary automatic medication delivery device assembly, before injection, with different dose settings, according to the invention.
Figure 3:
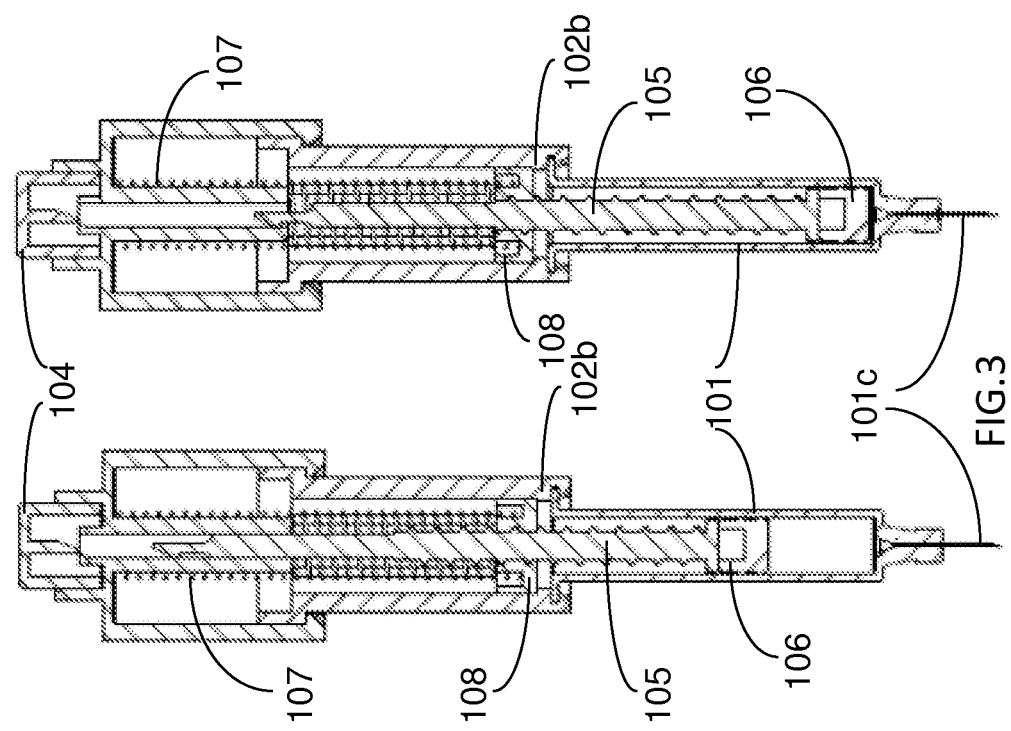
FIG. 3 shows cross-sectional views of the exemplary automatic medication delivery device assembly, after injection, with different dose settings, according to the invention.
Figure 4:
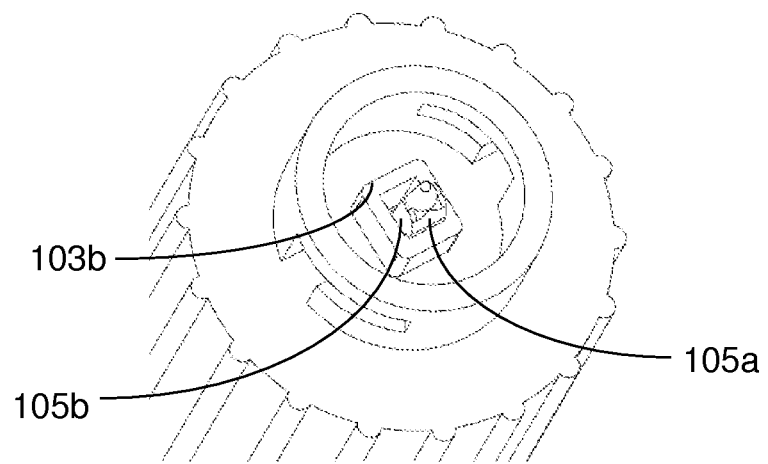
FIG. 4-6 are detailed views showing engagements between components of the exemplary automatic medication delivery device assembly according to the invention.
Figure 5:
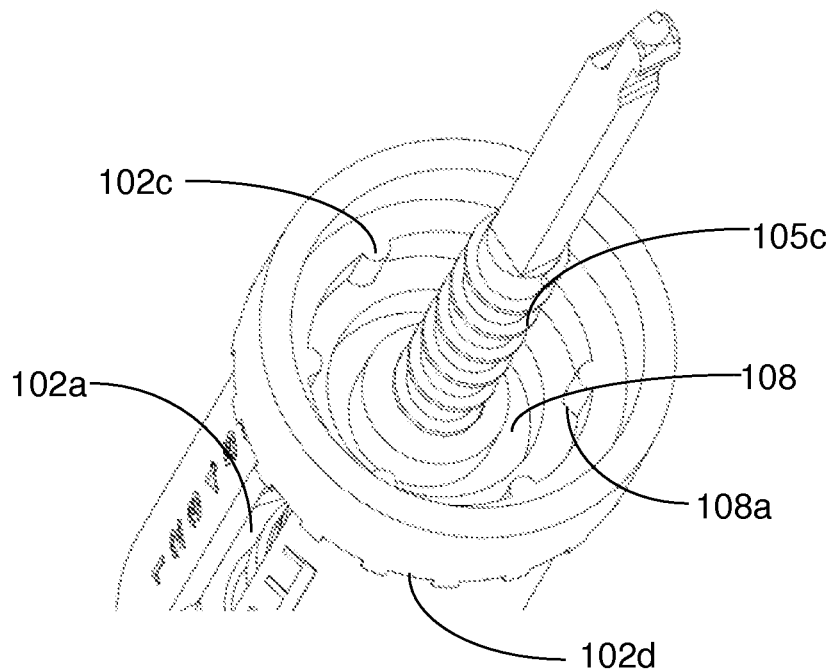
Figure 6:
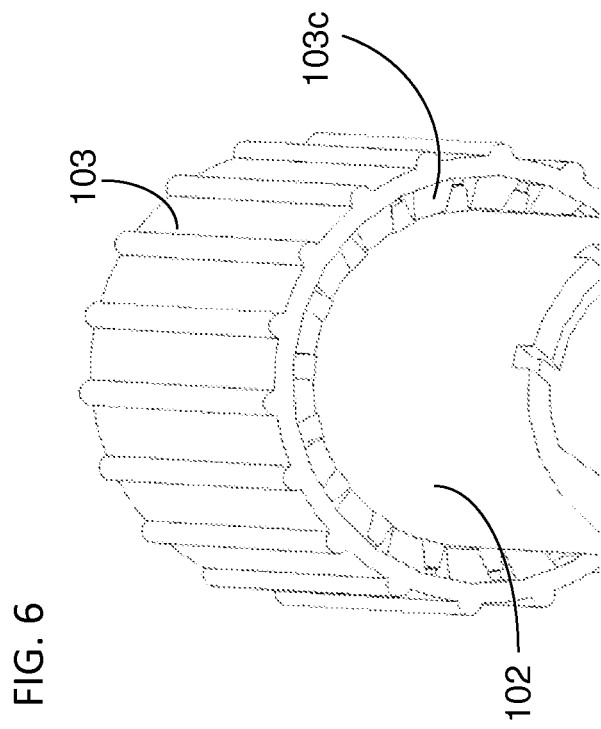
Figure 7:
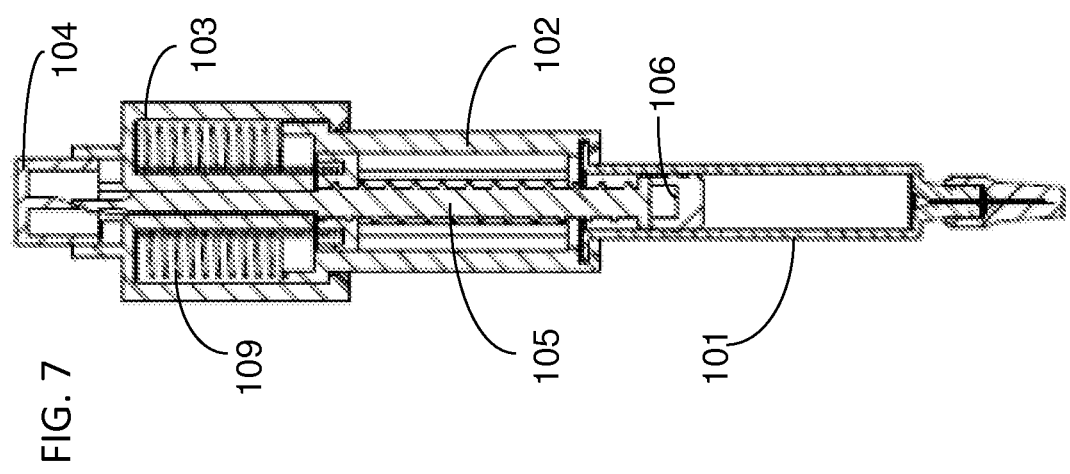
FIG. 7 shows cross-sectional view of another configuration of the exemplary automatic medication delivery device assembly according to the invention.

In this exemplary automatic medication delivery device assembly 10, a pre-filled syringe 101, as medication container, can be made of either glass or plastic materials. A push cap 104 is used to activate an automatic injection. The push cap 104 is engaged with a dialing cylinder 103, through a track 103a on the dialing cylinder 103. This engagement prevents accidental activation of the device before use. A dose setting window 102a being defined on a scale cylinder 102. During use, the dialing cylinder 103 is rotated to set the injection dose. With reference to FIG. 2, user sets the location of a stopping ring 108 in order to get the different injection doses. Meantime, before injection, the automatic medication delivery device assembly 10 is shown with a push rod 105 in a locked state, against biasing force of a driving spring 107, by a releasable latch mechanism formed between hook feature 105a on the push rod 105 and the dialing cylinder 103. The pre-filled syringe 101 is assembled together with the scale cylinder 102 through a flange feature 101b being defined on the pre-filled syringe 101. The liquid medication in the pre-filled syringe 101 is sealed by a piston 106 and an elastomeric needle shield 101a. With reference to FIG. 3, before injection, the needle shield 101a is removed and a needle 101c is exposed. During injection, the push cap 104 is pushed toward to the distal end of the device, a distally-directed tapered actuation feature 104a on the push cap 104 releases the releasable latch mechanism formed between hook feature 105a on the push rod 105 and the dialing cylinder 103. The push rod 105 is released and the driving spring 107 drives the stopping ring 108 together with the push rod 105 to move toward the distal end of the automatic medication delivery device 10. The piston 106 is pushed downward. Consequently, liquid medication in the pre-filled syringe 101 is injected from the device into patient's body. The stopping ring 108 stops at a landing feature 102b on the scale cylinder 102. The pre-set dose is delivered accordingly. FIG. 4 shows the engagements between the push rod 105 and the dialing cylinder 103. A rectangular shape channel feature 103b on the dialing cylinder 103 engages with flat surfaces 105b on the push rod 105. When user rotates the dialing cylinder 103, the push rod 105 rotates accordingly. The rectangular shape channel feature 103b further provides landing surface for the releasable hook feature 105a on the push rod 105. FIG. 5 shows engagements among the push rod 105, the stopping ring 108 and the scale cylinder 102. During the dose setting, user rotates the dialing cylinder 103 relative to the scale cylinder 102. Because of a thread feature 105c on the push rod 105, when the push rod 105 rotates, the stopping ring 108 moves up and down along axial of the device, through the thread engagement between the push rod 105 and stopping ring 108. The location of the stopping ring 108 can be viewed through viewing window 102a on the scale cylinder 102. Due to the constrain between groove feature 108a on the stopping ring 108 and rail feature 102c on the scale cylinder 102, the stopping ring 108 can only moves axially, but not radially along the push rod 105 during dose setting and during injection. FIG. 6 shows the engagement between the dialing cylinder 103 and the scale cylinder 102. In operation steps other than the dose setting step, the dialing cylinder 103 is always locked with the scale cylinder 102 together, through a tooth engagement between 103c on the dialing cylinder 103 and 102d on the scale cylinder 102, or some other mechanism which allows the components to be connected and disconnected from each other. This tooth-type lock engagement prevents free rotation of the dialing cylinder 103 and restrain the radial movement and back-threading of the push rod 105 during the entire injection process. During the dose setting step, user pushes the dialing cylinder 103 distally relative to the scale cylinder 102. Then, the locking engagement between 103c and 102d is disabled and the dialing cylinder 103 can be rotated relatively to the scale cylinder 102. After the dose setting, when there is absent of pushing force toward distal end of the automatic medication delivery device 10, the dialing cylinder 103 is biased proximally and re-engaged with the scale cylinder 102, due to the resilient force generated by the piston 106 or a separation spring 109 (shown on FIG. 7).

Figure 8:
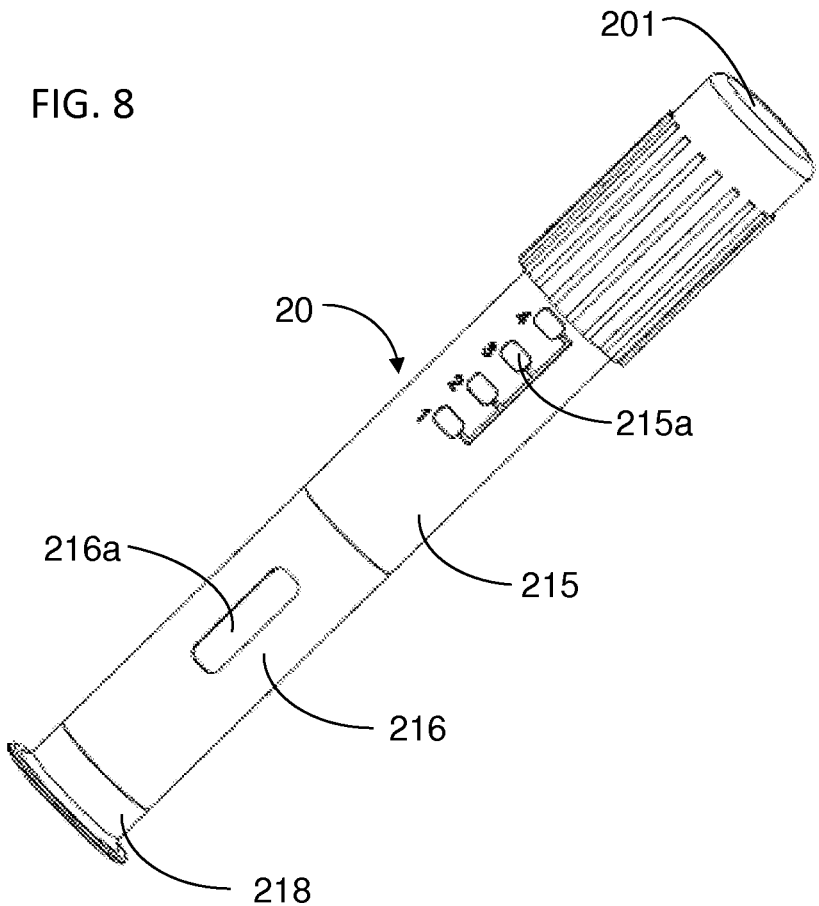
FIG. 8 is a perspective view of the first alternative automatic medication delivery device assembly according to the invention.
Figure 9:
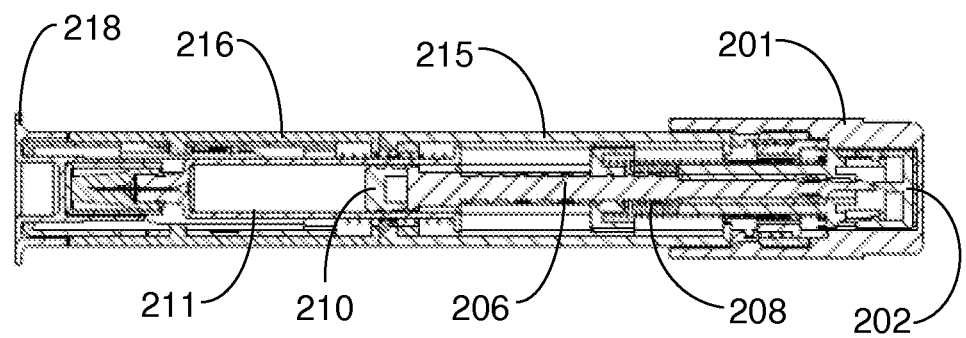
FIG. 9 is a cross-sectional view of the first alternative automatic medication delivery device assembly according to the invention.
Figure 10:
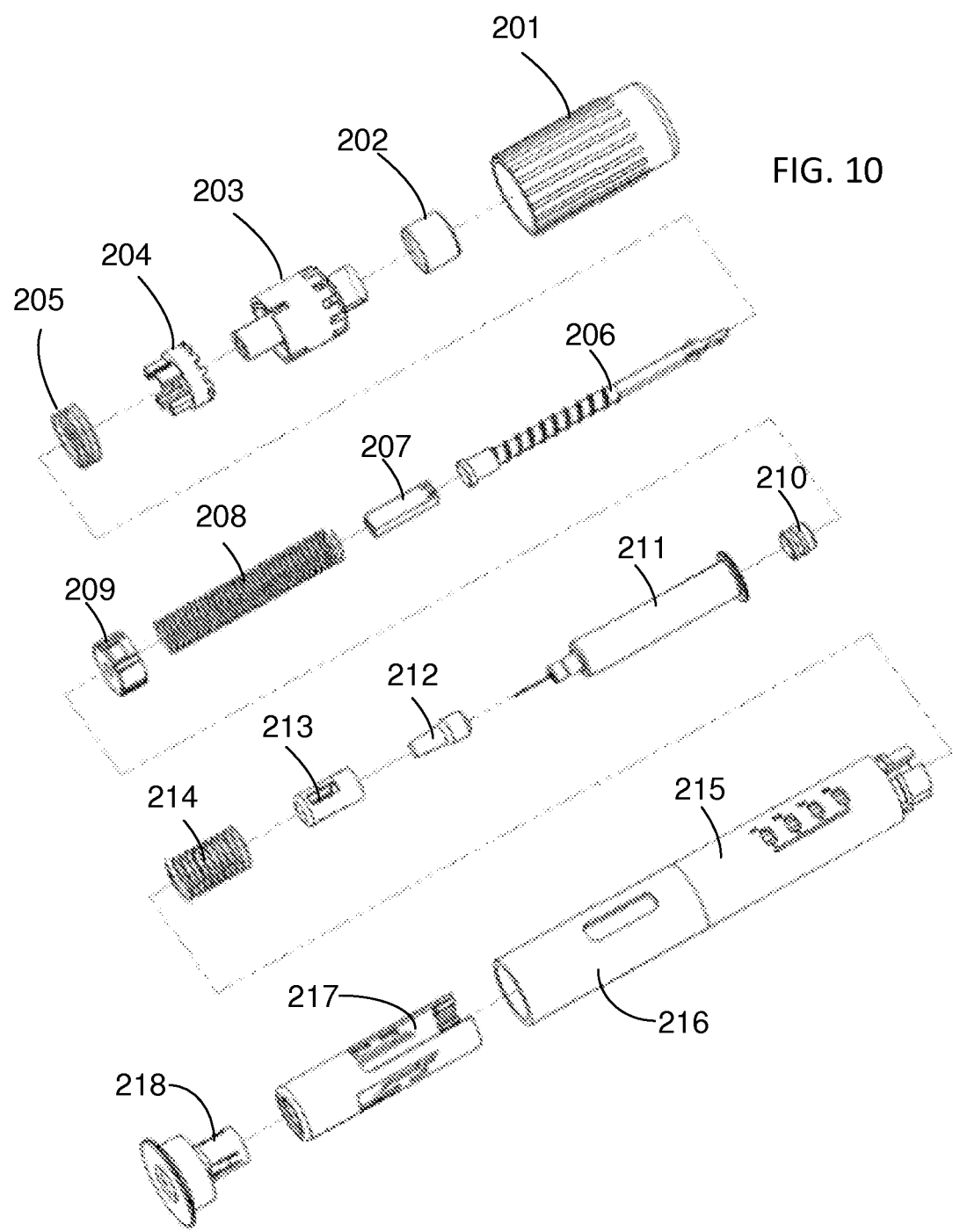
FIG. 10 is an exploded view of the first alternative automatic medication delivery device assembly according to the invention.
Figure 11:
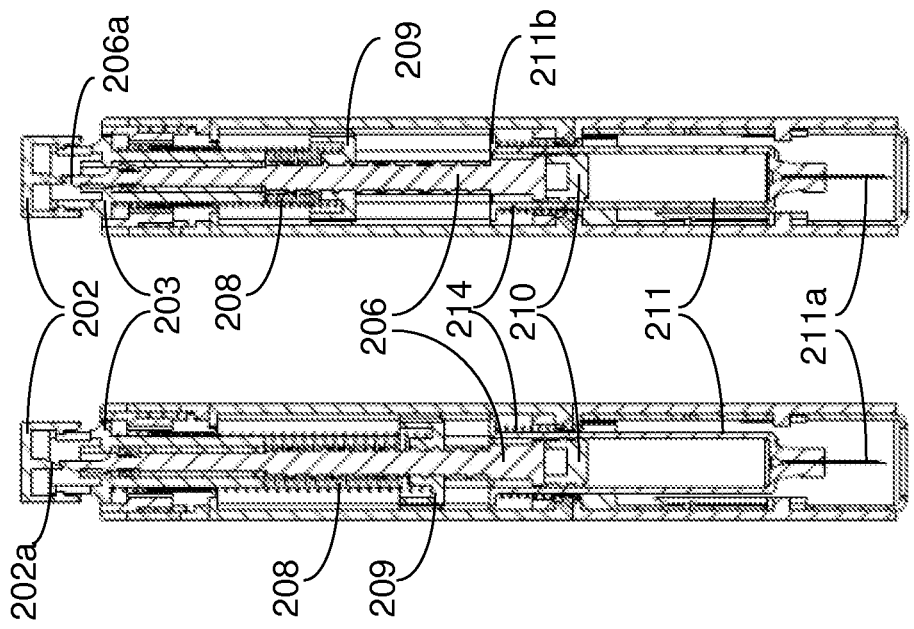
FIG. 11 shows cross-sectional views of the first alternative automatic medication delivery device assembly, before injection, with different dose settings, according to the invention.
Figure 12:
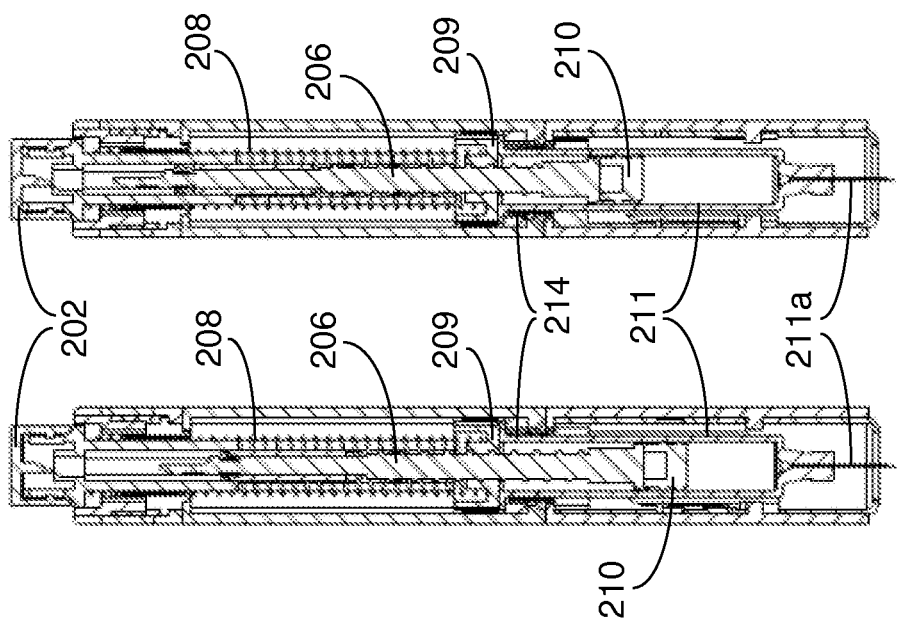
FIG. 12 shows cross-sectional views of the first alternative automatic medication delivery device assembly, after injection, with different dose settings, according to the invention.
Figure 13:
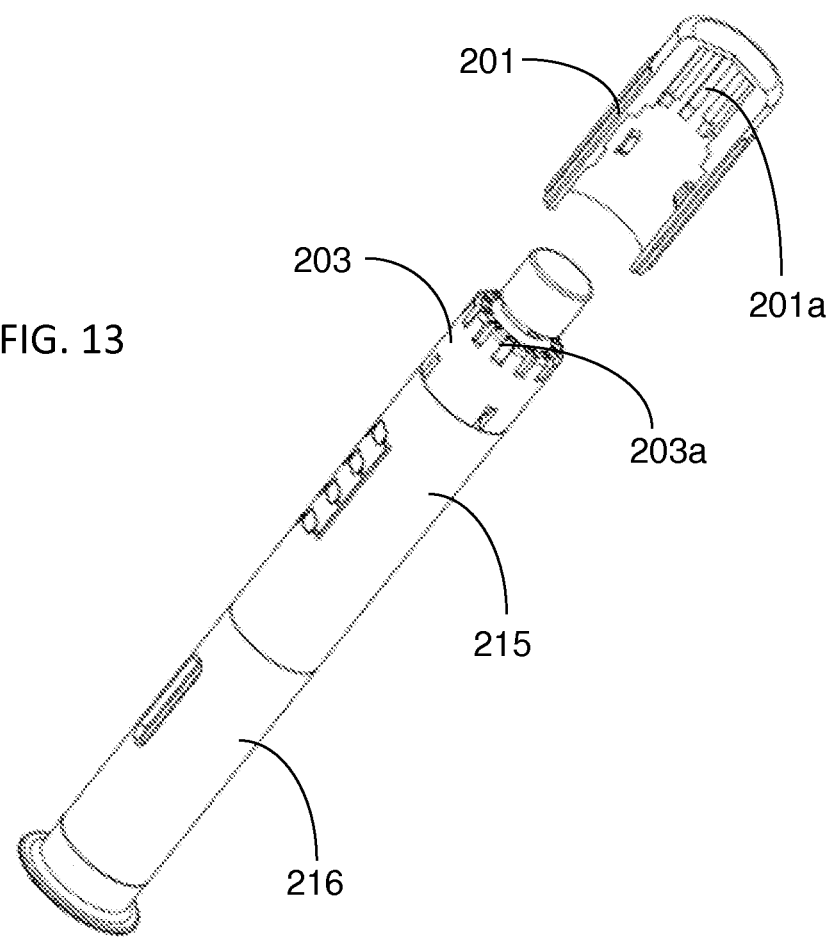
FIG. 13-20 show engagements between components of the first alternative automatic medication delivery device assembly according to the invention.
Figure 14:
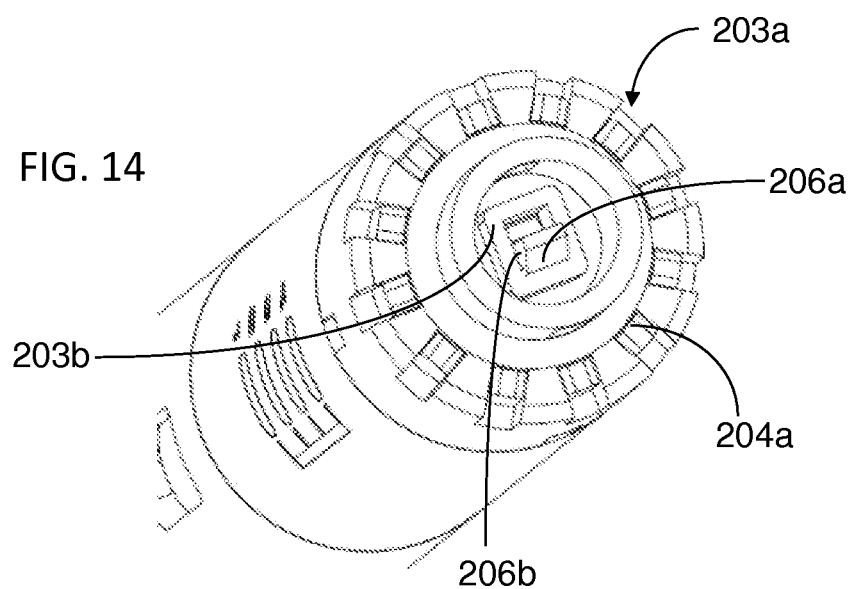
Figure 15:
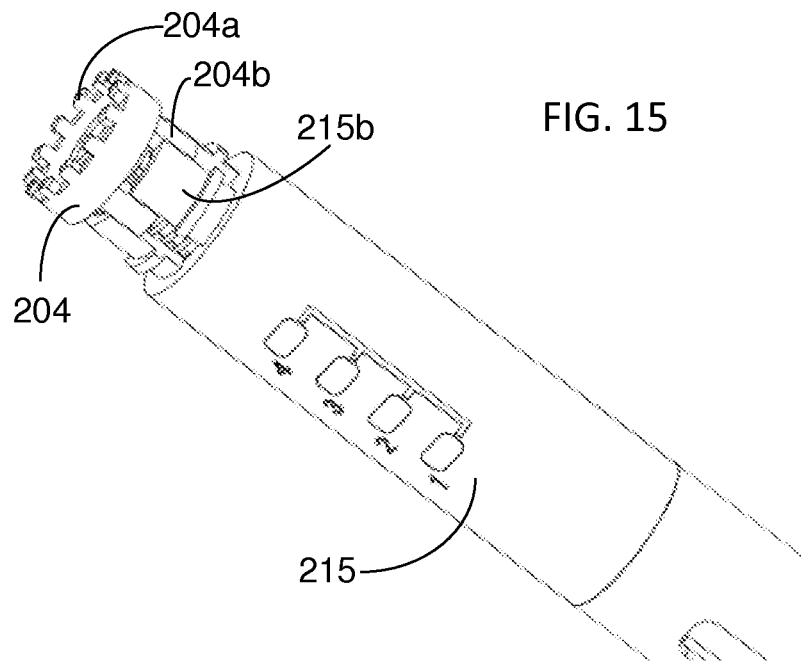
Figure 16:
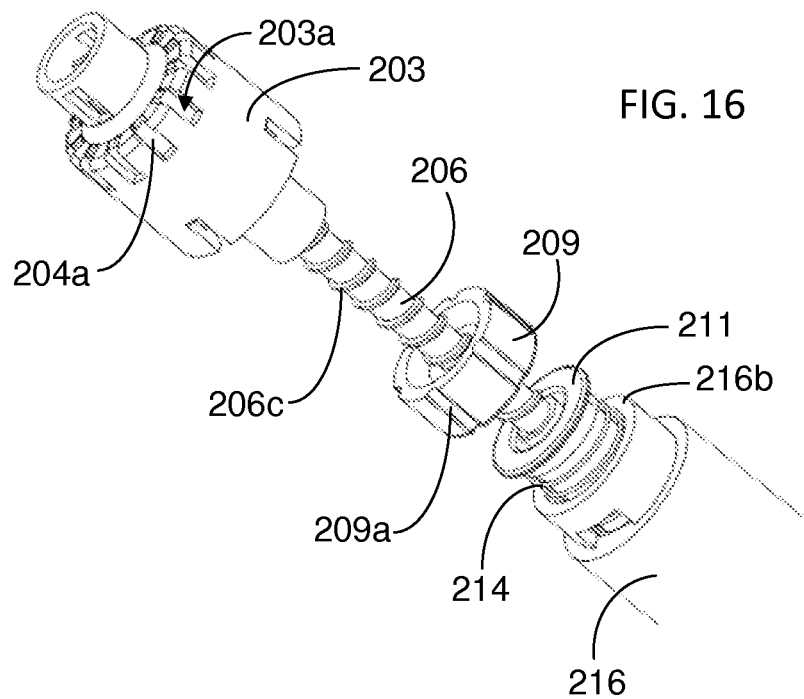
Figure 17:
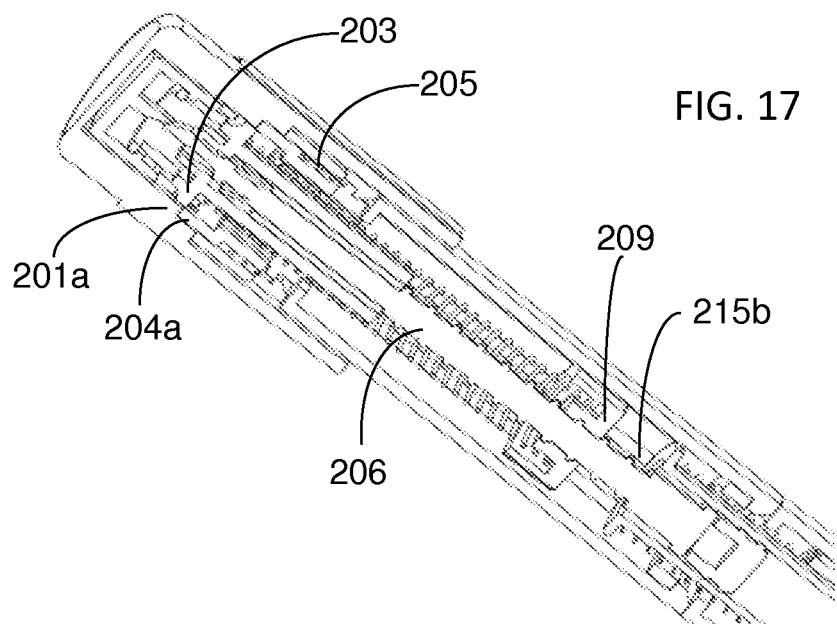
Figure 18:
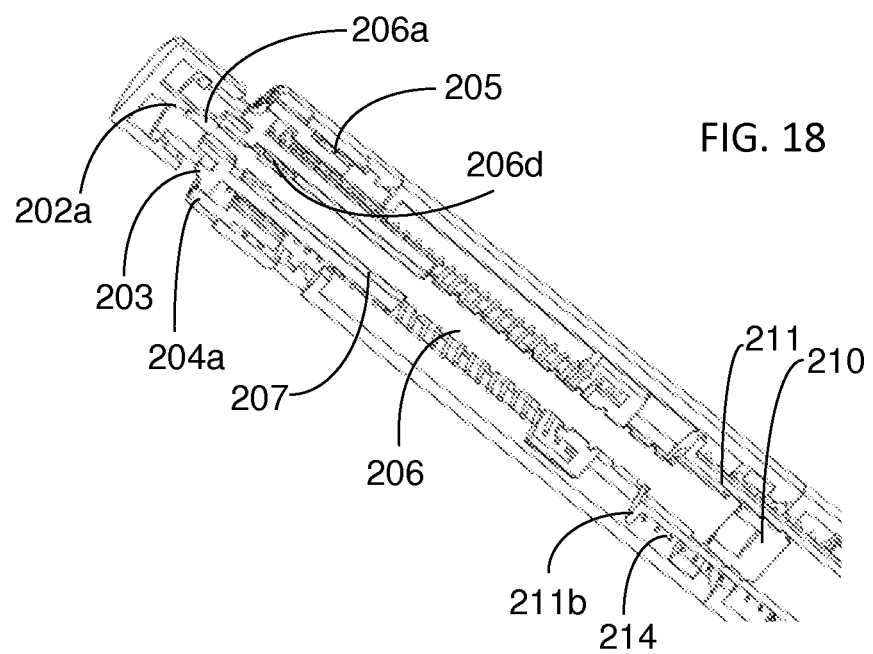
Figures 19, 20:
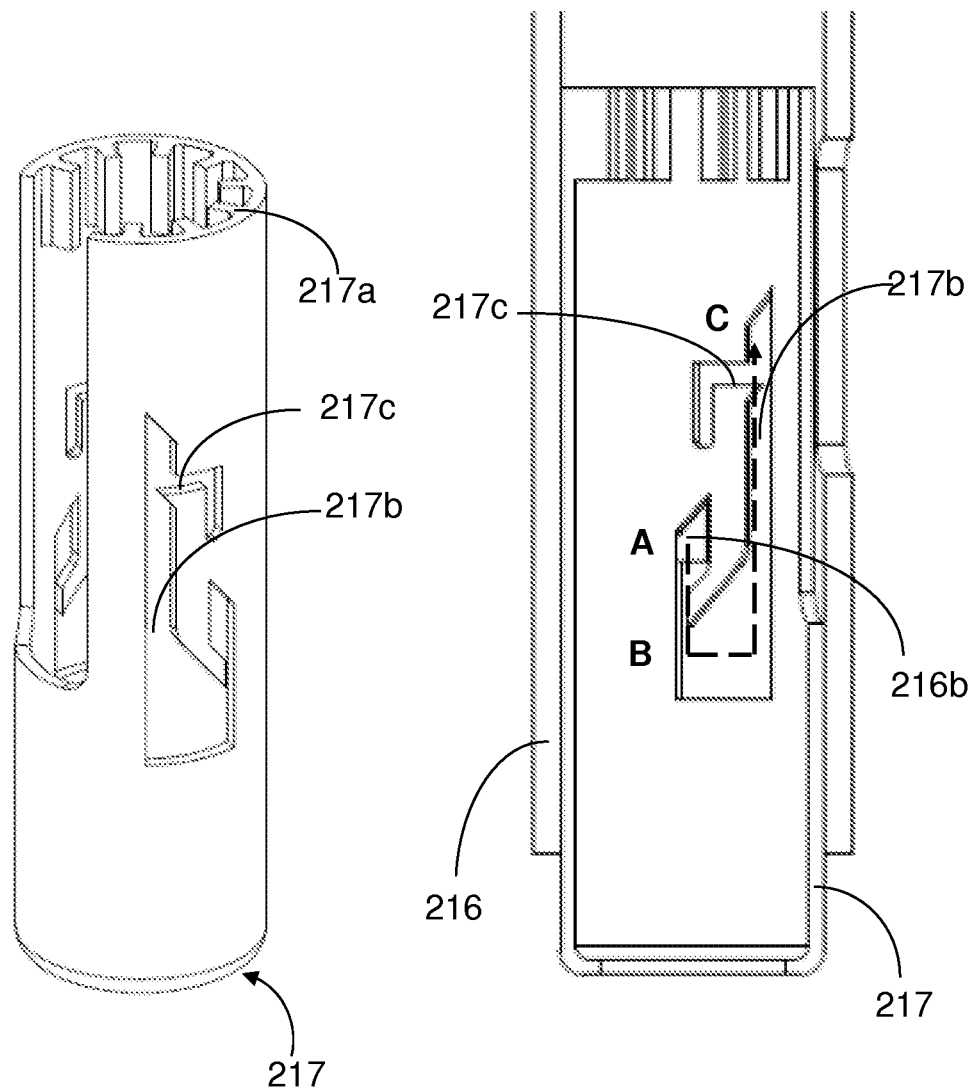
Figure 21:
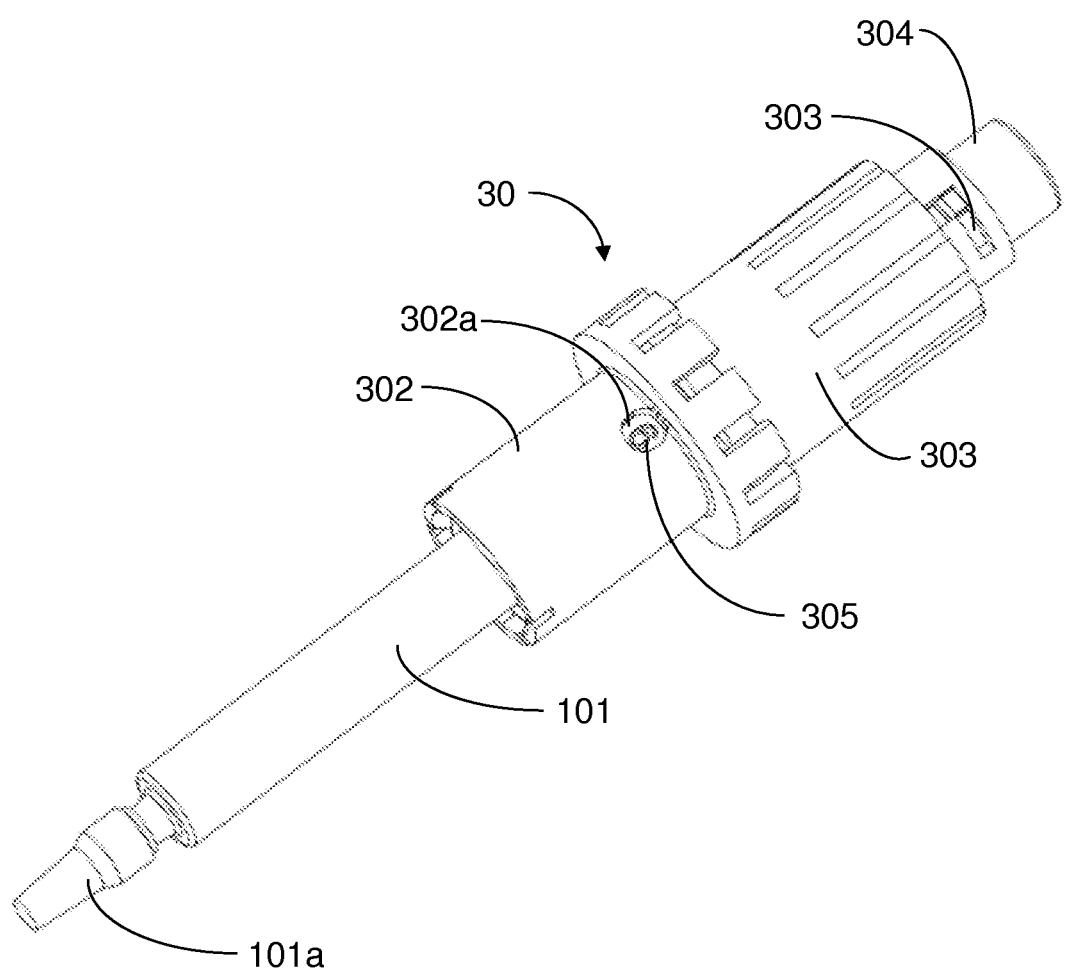
FIG. 21 is a perspective view of the second alternative automatic medication delivery device assembly according to the invention.

FIGS. 8-20 illustrate the construction and function mechanism of the first alternative automatic medication delivery device assembly 20 according to the invention. With reference to FIGS. 8 to 10, in this automatic medication delivery device assembly 20, a pre-filled syringe 211, as medication container, can be made of either glass or plastic materials. The liquid medication in the pre-filled syringe 211 is sealed by a piston 210 and an elastomeric needle shield 212. The elastomeric needle shield 212 and a needle shield shell 213 is placed at a the distal end of the syringe 211. A needle shield puller 218 is used to remove the needle shield 212 and the needle shield shell 213 before injection. A dialing cap 201 is used to set the injection dose. A push cap 202 is used to activate an automatic injection. The push cap 202 is engaged with a dialing cylinder 203. A dose setting area 215a is being defined on a scale cylinder 215. A viewing window 216a is being defined on a lower cylinder 216. During use, the dialing cap 201 is rotated to set the injection dose. After the dose setting, user removes the dialing cap 201 and exposes the push cap 202. With reference to FIG. 11, user sets the location of a stopping ring 209 along a push rod 206 in order to get the different injection doses. Meantime, before injection, the automatic medication delivery device assembly 20 is shown with the push rod 206 in a locked state, against biasing force of a driving spring 208, by a releasable latch mechanism formed between hook feature 206a on the push rod 206 and the dialing cylinder 203. Before injection, the needle shield 212 and the needle shield shell 213 are removed and a needle 211a is exposed. With reference to FIG. 12, during injection, the push cap 202 is pushed toward to the distal end of the device 20, a distally-directed tapered actuation feature 202a on the push cap 202 releases the releasable latch mechanism formed between hook feature 206a on the push rod 206 and the dialing cylinder 203. The push rod 206 is released and the driving spring 208 drives the stopping ring 209 together with the push rod 206 to move toward the distal end of the device 20. The stopping ring 209 meets the flange feature 211b on the pre-filled syringe 211. The piston 210 and also the prefilled syringe 211 are pushed downward. Consequently, the needle 211a is inserted in to skin and the liquid medication in the pre-filled syringe 211 is injected from the device into patient's body. FIG. 13 shows the engagement between the dialing cap 201 and the dialing cylinder 203. Rib feature 201a on the dialing cap 201 engages with open slot feature 203a on the dialing cylinder 203 when the two components are assembled together. When user rotates the dialing cap 201, the dialing cylinder 203 rotates accordingly. FIG. 14 shows the engagements among the dialing cylinder 203, the push rod 206 and a lock key 204. The rectangular channel feature 203b on the dialing cylinder 203 engages with the flat surfaces 206b on the push rod 206. When the dialing cylinder 203 is rotated, the push rod 206 rotates accordingly. The channel feature 203b further provides landing surface for the releasable hook feature 206a on the push rod 206. Key feature 204a on the lock key 204 engages into the slot feature 203a on the dialing cylinder 203 after the dialing cap 201 is removed. At this stage (also shown in FIG. 18), the dialing cylinder cannot be rotated anymore. At the stage shown in FIGS. 13 and 17, the rib feature 201a on the dialing cap 201 pushed down the key feature 204a on the lock key 204 so that the dialing cylinder 203 can be disengaged from the lock key 204 and rotated along with the dialing cylinder 201. An alternative configuration of dialing cap 201 can be provided without the rib feature 201a. In this case, the dialing cap still have the function to protect the push cap 202. However, user will not be able to use the dialing cap to set the dose. This can be useful when pharmacists or medical professionals prefer to pre-set the dose, using the dialing cap having rib feature 201a, for patients. Then, pharmacists or medical professionals replace the dialing cap having the rib feature 201a with the dialing cap having no rib feature 201a. As the result, patients will not be able to change the dose after the device is dispensed. Furthermore, the match between the rib feature 201a on the dialing cap 201 and the open slot feature 203a on the dialing cylinder 203 and the key feature 204a on the lock key 204 can be customized for different medications and/or different patients, just like the lock-key match. FIG. 15 shows the engagement between the lock key 204 and the scale cylinder 215. Leg feature 204b on the lock key 204 engages into slot feature 215b on the scale cylinder 215 and the leg feature 204b can move up and down along the slot feature 215b. FIG. 16 shows the engagement among the push rod 206, the stop ring 209 and the pre-filled syringe 211. During the dose setting, user rotates the dialing cap 201 and so the dialing cylinder 203 relative to the scale cylinder 215. Because of thread feature 206c on the push rod 206, when the push rod 206 rotates, the stopping ring 209 moves up and down along the push rod 206, through the thread engagement between the push rod 206 and the stopping ring 209. The location of the stopping ring 209 can be viewed through the viewing window 215a on the scale cylinder 215. Because of the constrain between groove feature 209a on the stopping ring 209 and rail feature 215b on the scale cylinder 215 (shown in FIG. 17), the stopping ring 209 can only moves axially, but not radially along the push rod 206, during dose setting and during injection. With reference to FIG. 17, a separation spring 205 is used to support the lock key 204. When the dialing cap 201 is assembled with the automatic medication delivery device 20, the lock key 204 is pushed toward to the distal end of the device and the separation spring 205 is compressed. Also shown on FIG. 17, a syringe spring 214 is placed between the flange feature 211b on the pre-filled syringe 211 and a needle protection sheath 217. During injection, the syringe spring 214 is compressed by the push rod 206 and the stopping ring 209. The movement of the pre-filled syringe, toward to the distal end of the device, stops at the landing face feature 216b on the lower cylinder 216. With reference to FIG. 18, after the dialing cap 201 is removed, the separation spring 205 pushes the lock key 204 toward to the proximal end of the automatic medication delivery device 20. The lock key 204 restrains the radial movement of the dialing cylinder 205 and the push rod 206 during injection. Also shown in FIG. 18, an extension sheath 207 is used to ensure the rectangular channel 203b on the dialing cylinder 203 always communicate with the feature 206b on the push rod 206 and restrain the radial movement of the push rod 206 during the entire injection. When the push rod 206 moves toward to the distal end of the device further enough, the extension sheath 207 is dragged out (telescoping) toward to the distal end of the automatic medication delivery device 20, through finger feature 206d on the push rod 206. FIG. 19 shows the needle protection sheath 217. Flat surface feature 217a on the needle protection sheath 217 is used to support the syringe spring 214. Track feature 217b being defined on the needle protection sheath 217 is used to control the position of the needle protection sheath 217. FIG. 20 shows the engagement between the lower cylinder 216 and the needle protection sheath 217. A key feature 216b on the lower cylinder 216 is engaged in the track 217b on the needle protection sheath 217. The arrowed dash line shows the movement of the key feature 216b relative to the track 217b. Before injection, the key feature 216b is at position A.

During injection, the automatic medication delivery device is pushed against the skin on user and the key feature 216b moves to position B relative to the track 217b. After injection, when user removes the automatic medication delivery device 20 away from the skin, the syringe spring 214 pushes the needle protection sheath 217 to extend out toward the distal end of the device 20. The key feature 216b moves to position C relative to the track 217b. The extended portion of the needle protection sheath 217 covers the needle 211a after injection. The block feature 217c on the needle protection sheath 217 locks the needle protection sheath 217 in an extended position.

Figure 22:
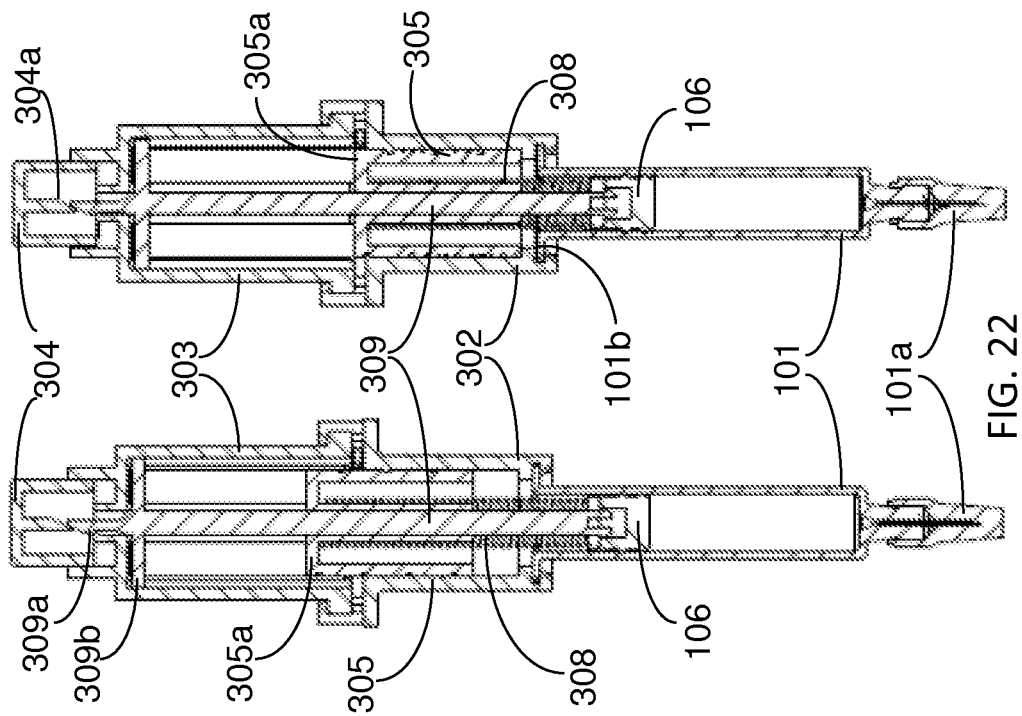
FIG. 22 shows cross-sectional views of the second automatic medication delivery device assembly, before injection, with different dose settings, according to the invention.
Figure 23:
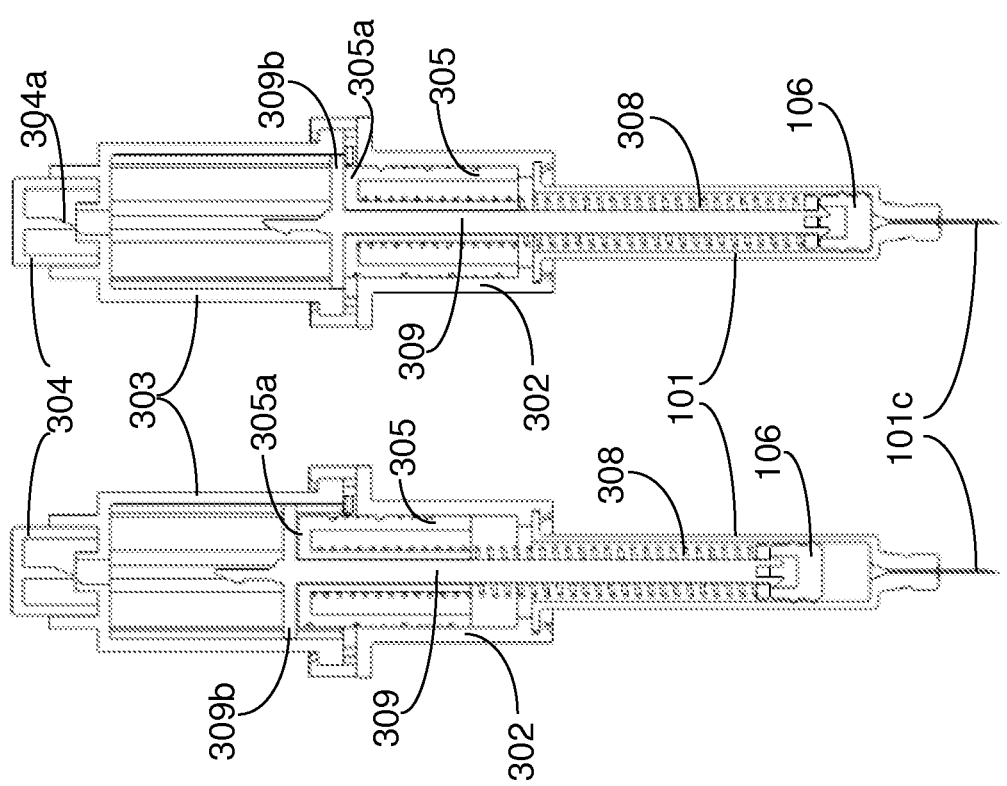
FIG. 23 shows cross-sectional views of the second automatic medication delivery device assembly, after injection, with different dose settings, according to the invention.
Figure 24:
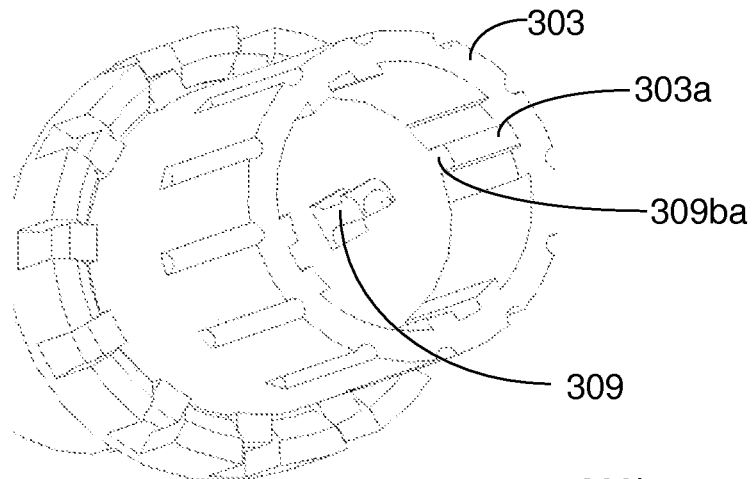
FIG. 24-26 show engagements between components of the second alternative automatic medication delivery device assembly according to the invention.
Figure 25:
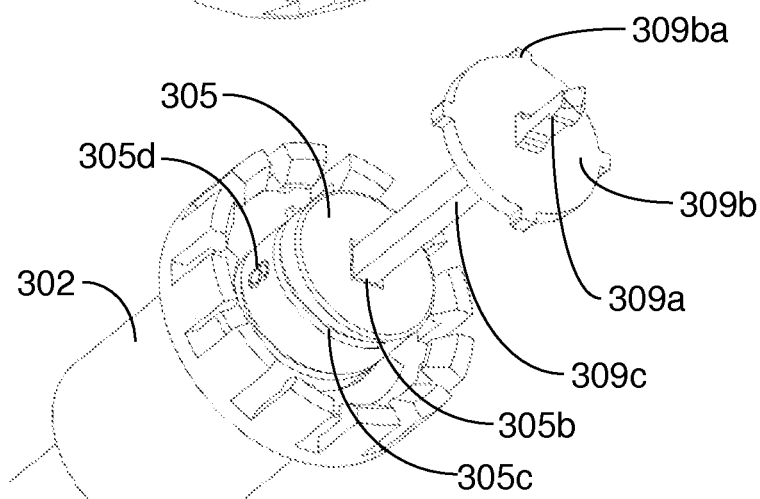
Figure 26:
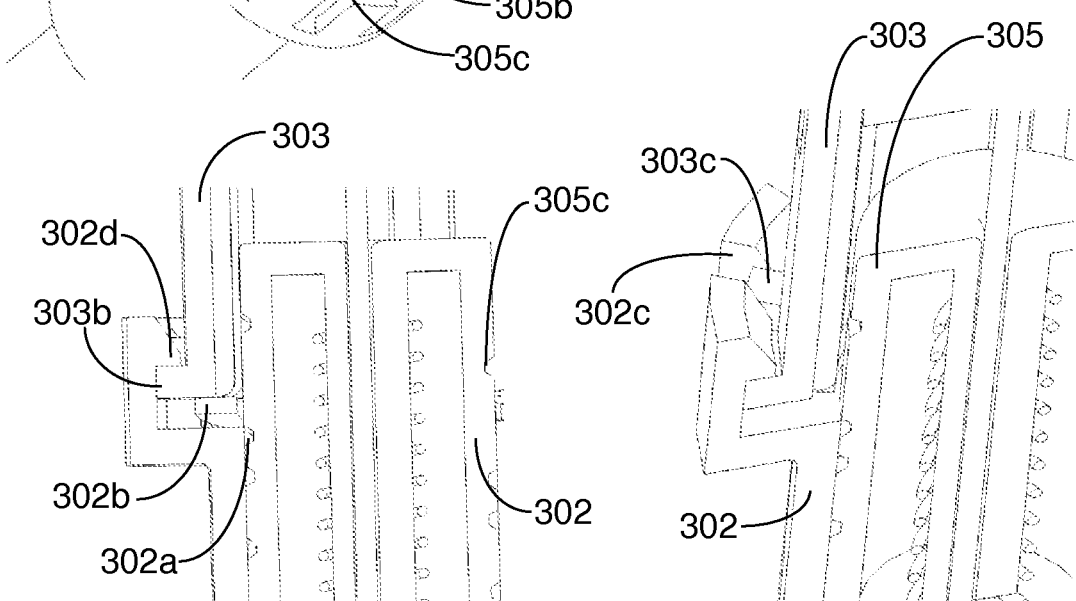
Figure 29:
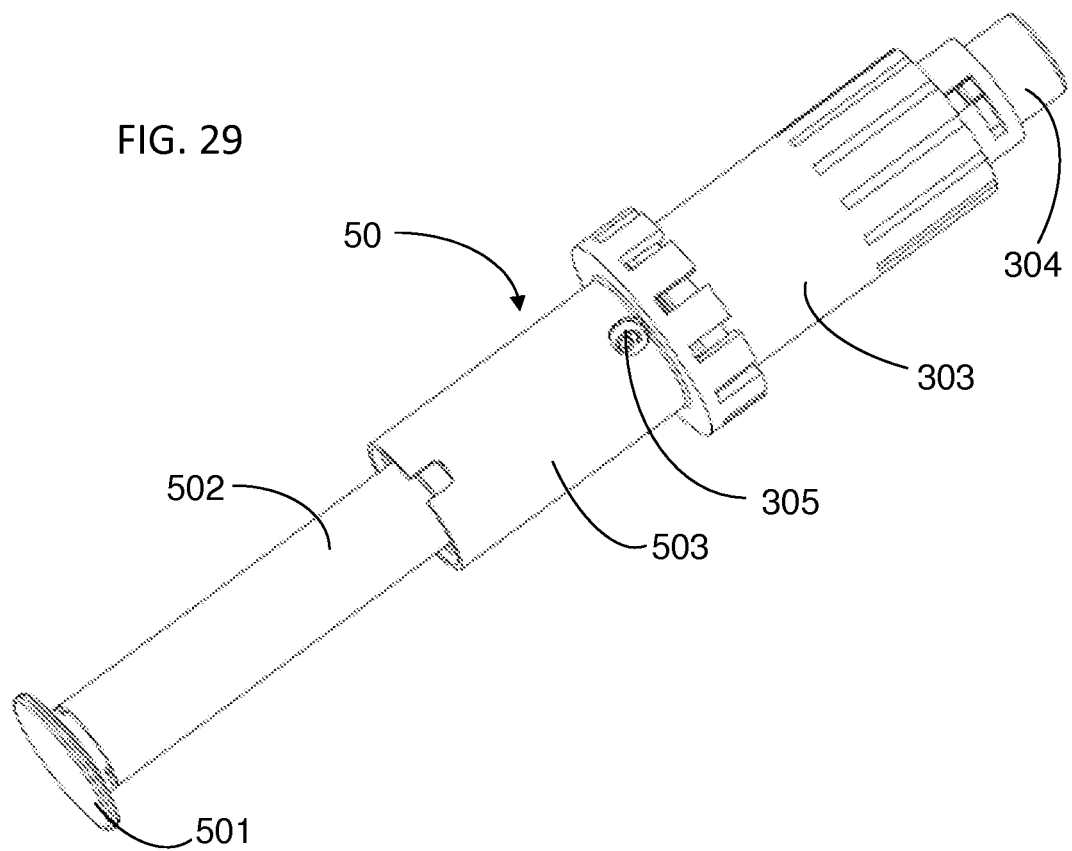
FIG. 29 is a perspective view of the fourth alternative automatic medication delivery device assembly according to the invention.

FIGS. 21-26 illustrate the construction and function mechanism of the second alternative automatic medication delivery device assembly 30 according to the invention. In this automatic medication delivery device assembly 30, the pre-filled syringe 101 is used as medication container. A push cap 304 is used to activate an automatic injection. The push cap 304 is engaged with a dialing cylinder 303, through a track 303a on the dialing cylinder 303. This engagement prevents accidental activation of the device before use. A dose setting window 302a being defined on a lower cylinder 302. A scale cylinder 305 has dose scale mark on it. During use, the dialing cylinder 303 is rotated to set the injection dose. With reference to FIG. 22, user sets the location of the scale cylinder 305 in order to get different injection doses. Meantime, before injection, the automatic medication delivery device assembly 30 is shown with a push rod 309 in a locked state, against biasing force of a driving spring 308, by a releasable latch mechanism formed between the dialing cylinder 303 and hook feature 309a on the push rod 309. The pre-filled syringe 101 is assembled together with the lower cylinder 302 through the flange feature 101b being defined on the pre-filled syringe 101. The liquid medication in the pre-filled syringe 101 is sealed by a piston 106 and an elastomeric needle shield 101a. With reference to FIG. 23, before injection, the needle shield 101a is removed and the needle 101c is exposed. During injection, the push cap 304 is pushed toward to the distal end of the device 30, a distally-directed tapered actuation feature 304a on the push cap 304 releases the releasable latch mechanism formed between the dialing cylinder 303 and hook feature 309a on the push rod 309. The push rod 309 is released and the driving spring 308 drives the push rod 309 to move toward the distal end of the device 30. The piston 106 is pushed downward. A disc feature 309b on the push rod 309 stops at the landing feature 305a on the scale cylinder 305 and the movement of the push rod 309 is limited. Consequently, liquid medication in the pre-filled syringe 101 is injected into patient's body. FIG. 24 shows the engagements between the push rod 309 and the dialing cylinder 303. The tongue feature 309ba on the disc feature 309b on the push rod 309 engages with the groove feature 303a on the dialing cylinder 303. When user rotates the dialing cylinder 303, the push rod 309 rotates accordingly. FIG. 25 shows the engagements between the push rod 309 and the the scale cylinder 305. During the dose setting, user rotates the dialing cylinder 303 relative to the lower cylinder 302. Because of the engagement between the push rod 309 and the dialing cylinder 303, the rotation of dialing cylinder 303 cause the rotation of the push rod 309. When the push rod 309 rotates, the scale cylinder 305 rotates accordingly because of the engagement between the rectangular channel 305b on the scale cylinder 305 and the flat engagement surface 309c on the push rod 309. The thread feature 305c on the scale cylinder 305 engages with the thread key feature 302a on the lower cylinder 302. When the scale cylinder 305 rotates, the scale cylinder 305 also moves up and down along the axial of the push rod 309, through the thread engagement between the scale cylinder 305 and the lower cylinder 302. The location of the scale cylinder 305 can be viewed through the viewing window 202a on the lower cylinder 302. The dose mark feature 305d on the scale cylinder 305 can be used for dose indication. FIG. 26 shows the engagements among the dialing cylinder 303, the scale cylinder 306 and the lower cylinder 302. In operation steps other than the dose setting step, the dialing cylinder 303 is always locked with the lower cylinder 302 together, through the tooth engagement between 303c on the dialing cylinder 303 and 302c on the lower cylinder 302. During the dose setting step, user pushes down the dialing cylinder 303 relatively to the lower cylinder 302. Then, the tooth-type locking engagement between 303c and 302c is disabled and the dialing cylinder 303 can be rotated relatively to the lower cylinder 302.

After the dose setting, when there is absent of pushing down force, the dialing cylinder 303 is pushed up and re-engaged with the scale cylinder 302, due to the resilient force generated by the resilient finger feature 302b on the lower cylinder 302. The upward movement of the dialing cylinder 303 is stopped by the flange feature 303b on the dialing cylinder 303 and the hook feature 302d on the lower cylinder 302.

FIGS. 27-28 illustrate the construction and function mechanism of the third alternative automatic medication delivery device assembly 40 according to the invention. The dose setting mechanism and activation mechanism of the automatic medication delivery device 40 is the same as those of the automatic medication delivery device 30. In this automatic medication delivery device assembly 40, a pre-filled cartridge 404 is used as medication container. The pre-filled cartridge 404 is assembled together with a lower cylinder 403 through a cartridge sheath 402. The proximal end of the cartridge sheath has the slot feature 402a, which is used to engage with the snap figure feature 403a on the lower cylinder 403. The distal end of the cartridge sheath 402 has the thread feature 402b, which is used to engage a double-ended pen needle 401.

Figure 30:
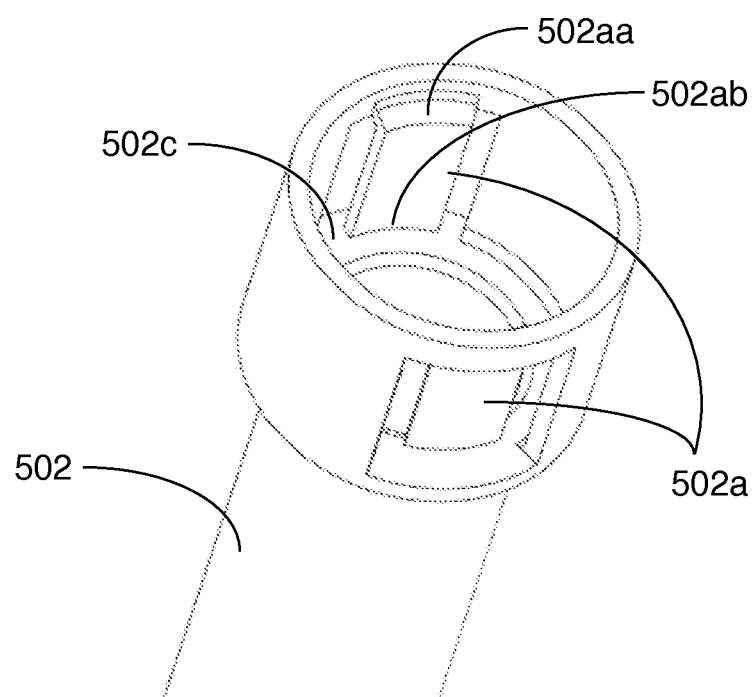
FIG. 30 is a perspective view of a component used in the fourth alternative automatic medication delivery device assembly according to the invention.
Figure 31:
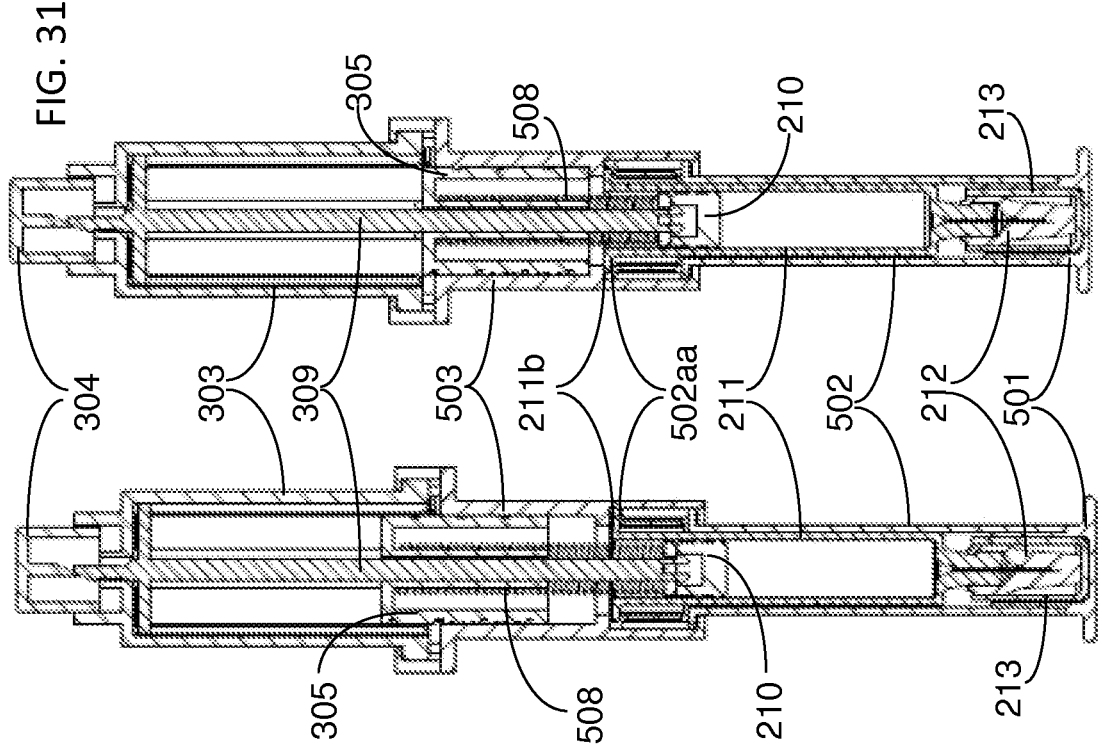
FIG. 31 shows cross-sectional views of the fourth alternative automatic medication delivery device assembly, before injection, with different dose settings, according to the invention.
Figure 32:
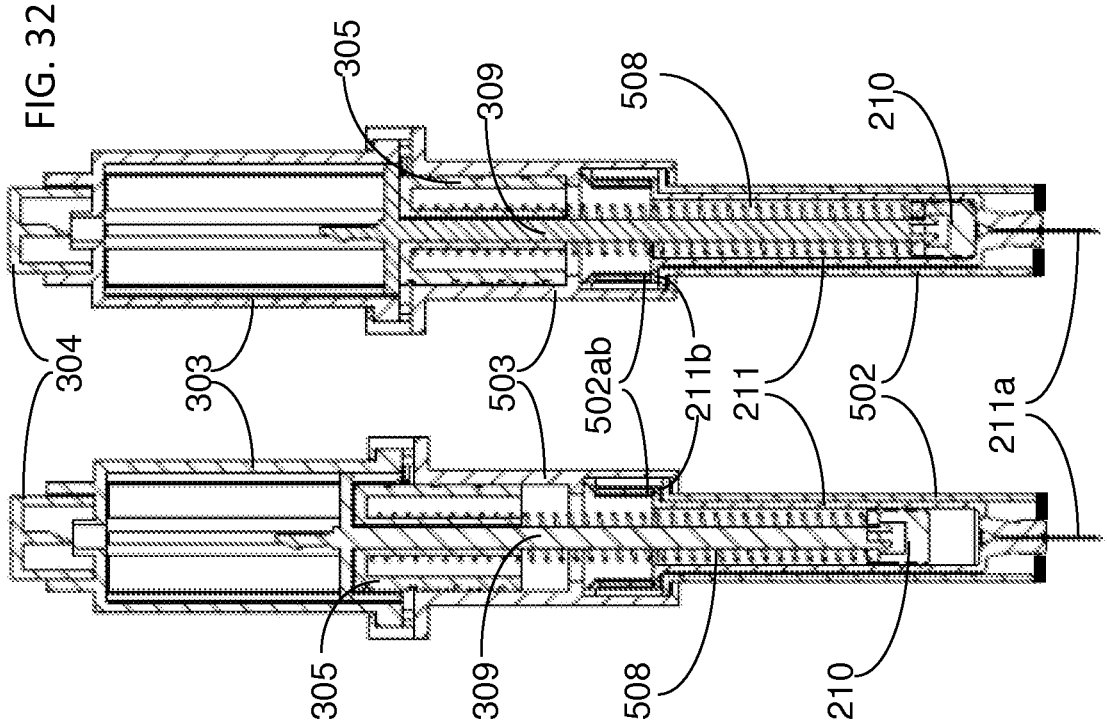
FIG. 32 shows cross-sectional views of the fourth alternative automatic medication delivery device assembly, after injection, with different dose settings, according to the invention.
Figure 35:
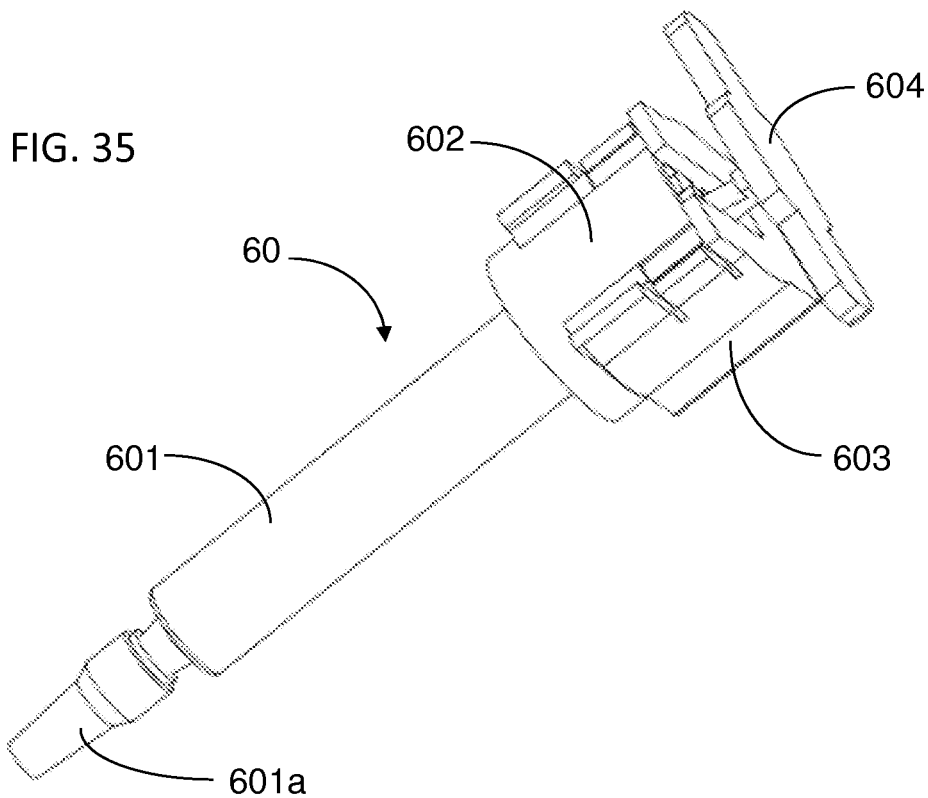
FIG. 35 is a perspective view of the fifth alternative automatic medication delivery device assembly according to the invention.

FIGS. 29-34A illustrate the construction and function mechanism of the fourth alternative automatic medication delivery device assembly 50 according to the invention. The dose setting mechanism and activation mechanism of the automatic medication delivery device 50 is the same as those of the automatic medication delivery device 30. In this automatic medication delivery device assembly 50, the pre-filled syringe 211 is used as medication container. Furthermore, an automatic needle insertion mechanism is introduced in the automatic medication delivery device assembly 50. A syringe housing 502 is used, together with a lower cylinder 503, to host the pre-filled syringe 211. A needle shield puller 501 is used to remove the needle shield 212 and the needle shield shell 213 before injection. FIG. 30 shows the syringe housing 502. There are one-way, bendable, positioning fingers 502a being defined on the syringe housing 502. The length of the positioning fingers 502a is more than the length that required to disengage the needle shied 212 from the syringe 211. The proximal end 502aa of the positioning FIGS. 502a is used to support the flange feature 211b on the pre-filled syringe 211, before injection. FIG. 31 shows the automatic medication delivery device 50 with different dose setting before injection. Before injection, the flange feature 211b on the pre-filled syringe 211 is rested at the proximal end 502aa of the positioning fingers 502a. To further support the pre-filled syringe 211 to be placed at the proximal end 502aa before injection, an optional supporting spring (not show) can be placed between the syringe flange 211b and surface 502c on the syringe housing 502. In the case that the syringe 211 moves a short distance distally during the needle shield removal, the supporting spring will push the syringe 211 to move back to the proximal end 502aa. Meantime, the counter force generated by the optional supporting spring is less than the force generated by a driving spring 508 so that the distal toward movement of the syringe 211 won't be impeded by the optional support spring. FIG. 32 shows the automatic medication delivery device 50 with different dose setting after injection. It can be seen that during injection, the flange feature 211b on the pre-filled syringe 211 is placed at the distal end 502ab of the positioning fingers 502a when a driving spring 508 pushes the piston 210 and the pre-filled syringe 211 toward to the distal end of the automatic medication delivery device 50. Because the barrel of the pre-filled syringe 211 won't contact injection site during the injection, there is no resistance for the flange feature 211b to move to the distal end 502ab of the positioning fingers 502a. FIG. 33 shows syringe housing 512, as an alternative to syringe housing 502. The syringe housing 512 has lock key feature 512a and finger feature 512b. The syringe housing 512 engages with a protection ring 513. Before injection, shown as FIG. 34, the axial movement of the protection ring 513 is blocked by the lock key feature 512a on the syringe housing 512, and the support finger feature 513a on the protection 513 prevents the syringe 211 to move distally. When user is ready for injection, user rotates the protection ring 513 to release position. At the release position, the protection ring can move distally. As shown in FIG. 34A, after injection, both the syringe 211 and the protection ring 513 to move distally, and the position of syringe 211 is stationed by the finger feature 512b.

Figure 36:
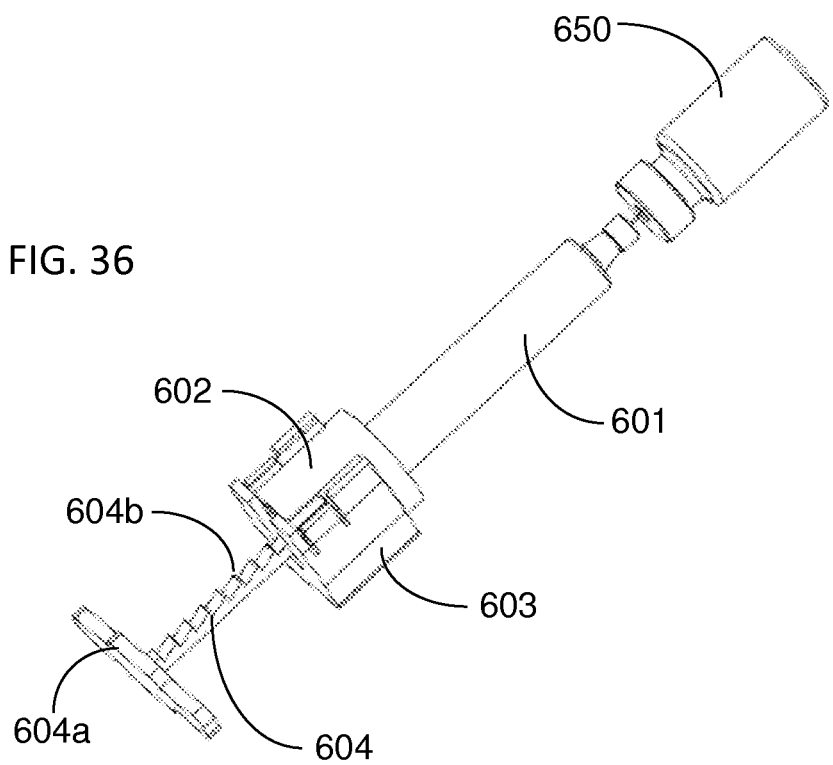
FIG. 36 is a perspective view of the fifth alternative automatic medication delivery device assembly used together with a medication containing vial, according to the invention.
Figure 37:
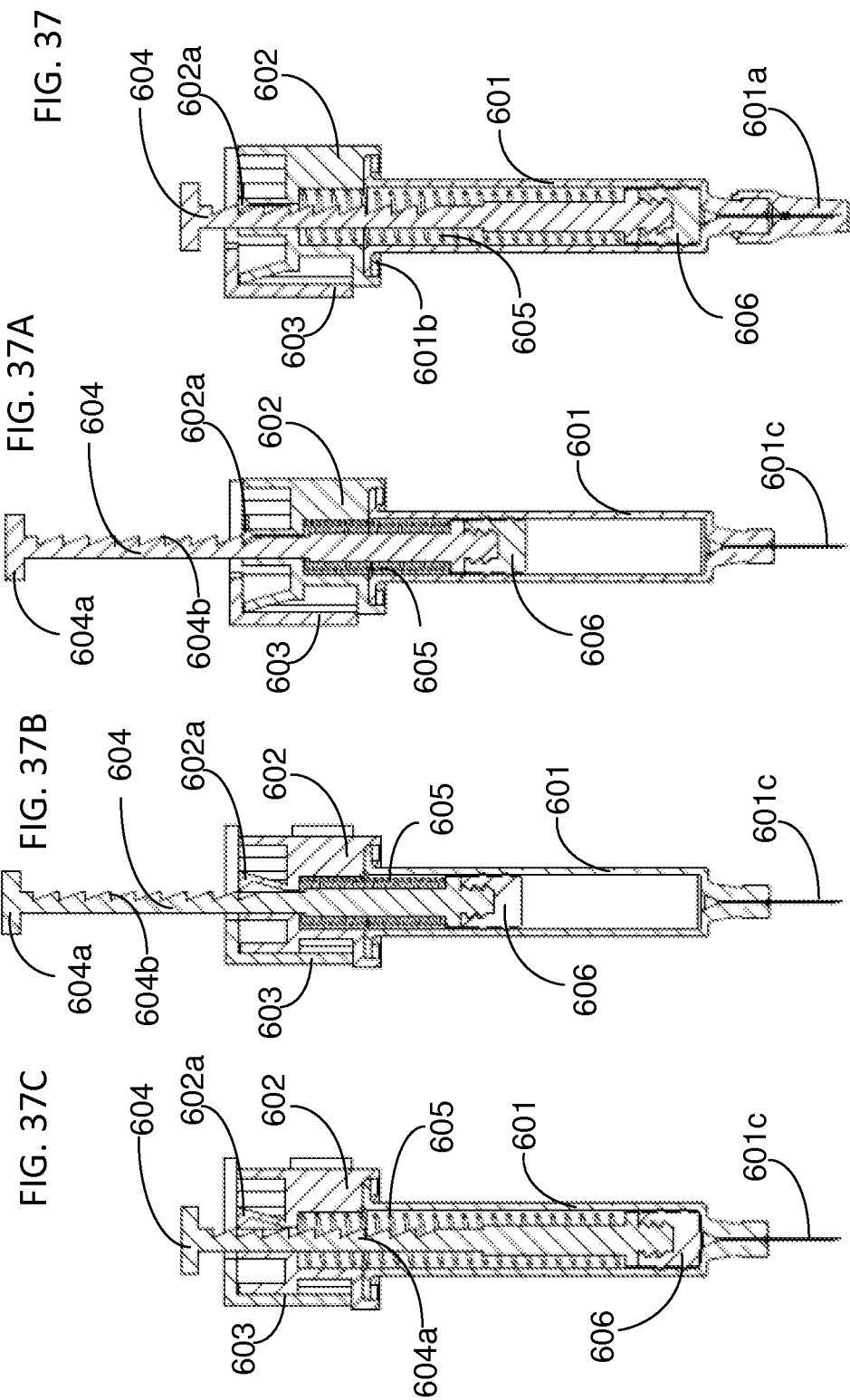
Figure 38:
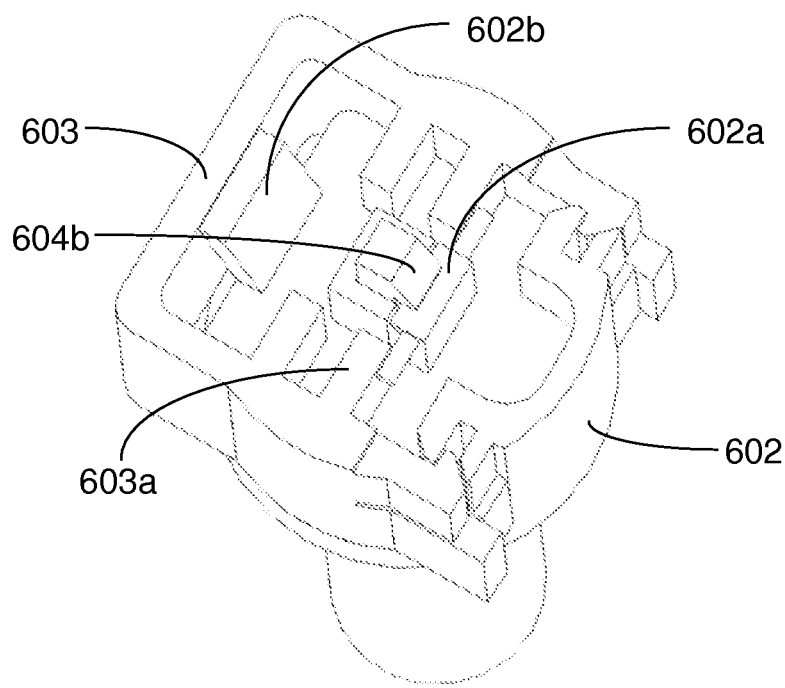
FIGS. 38 and 39 show engagements between components of the fifth alternative automatic medication delivery device assembly according to the invention.
Figure 39:
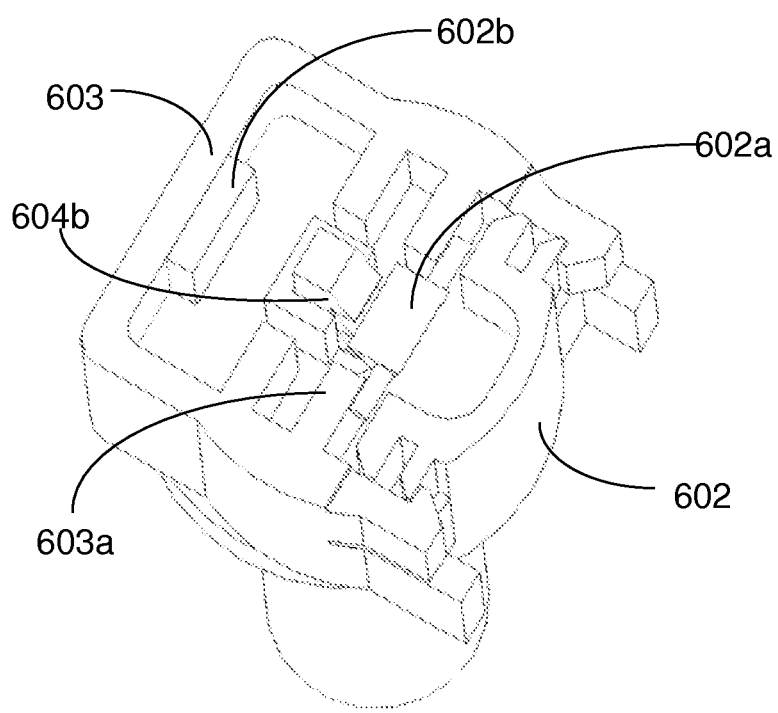

FIGS. 35-39 illustrate the construction and function mechanism of the fifth alternative automatic medication delivery device assembly 60 according to the invention. In this exemplary automatic medication delivery device assembly 60, a syringe 601, as medication container, can be made of either glass or plastic materials. A needle shield (or needle cap) 601a is placed at a the distal end of the syringe 601. A push button 603 is used to activate an automatic injection. The push button 603 is engaged with a connector 602. With reference to FIG. 36, user first removes the needle shield 601a. Then, user pulls a push rod 604 proximally and draws medication into the syringe 601 from vial 650. With reference to FIGS. 37 to 37C, the connector 602 is assembled with syringe 601 through a flange feature 601b on the syringe 601. Before injection, a driving spring 605 is in extended stage and a piston 606 is located at the distal end of the automatic medication delivery device 60. To draw medication into the syringe 601, user pulls the push rod 604, through the finger flange feature 604a on the push rod 604, toward to the proximal end of the automatic medication delivery device 60. The piston 606 is moved toward to the proximal end of the automatic medication delivery device 60 accordingly. Blocking feature 602a on the connector 602 engages with a series of teeth feature 604b on the push rod 604 in order to block the movement of the push rod 604 toward distal end of the device 60, which is driven by the driving spring 605. The teeth feature 604a on the push rod 604 is used to set different injection doses. A dose marking can be placed on the push rod 604 for assisting the dose setting. During injection, the push button 603 is pushed inward to the push rod 604, and the blocking feature 602a on the connector 602 is pushed outward from the push rod 604 accordingly (shown in FIG. 37B). The engagement between blocking feature 602a and the teeth feature 604b is disabled. Then, the push rod 604 is released and the driving spring 605 drives the the push rod 604 to move toward the distal end of the device 60. The piston 606 is pushed downward. Consequently, liquid medication in the syringe 601 is injected into patient's body. FIGS. 38 and 39 show the engagements among the push rod 604, the connector 602 and the push button 603. Before injection, the teeth feature 604b on the push rod 604 is engaged with the blocking feature 602a on the connector 602. A bendable finger feature 602b on the connector 602 biases the push button 603 outward relative to the push rod 604. As shown in FIG. 39, during injection, user pushes the push button 603 toward to the push rod 604. A flat feature 603a on the push button 603 pushes the blocking feature 602a on the connector 602 outward in order to release the push rod 604 for injection.

Figure 40:
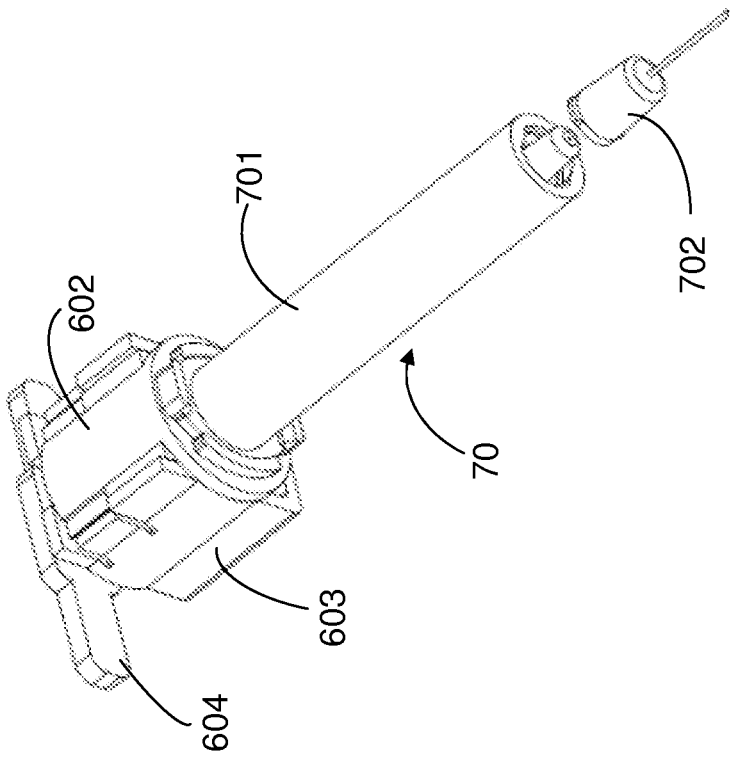
FIG. 40 is a perspective view of the sixth alternative automatic medication delivery device assembly according to the invention.
Figure 41:
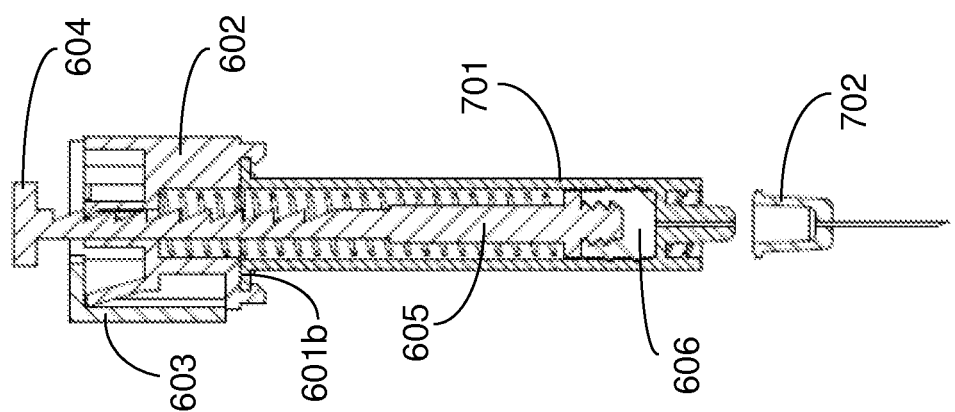
FIG. 41 is a cross-sectional view of the sixth alternative automatic medication delivery device assembly according to the invention.

FIGS. 40 and 41 illustrate the construction and function mechanism of the sixth alternative automatic medication delivery device assembly 70 according to the invention. The dose setting mechanism and activation mechanism of the automatic medication delivery device 70 is the same as those of the automatic medication delivery device 60. In this automatic medication delivery device assembly 70, a luer-lock syringe 701 is used as medication container. The luer-lock syringe 701 is assembled together with the connector 602. The distal end of the luer-lock syringe connects to a luer-lock needle 702.

Figure 42:
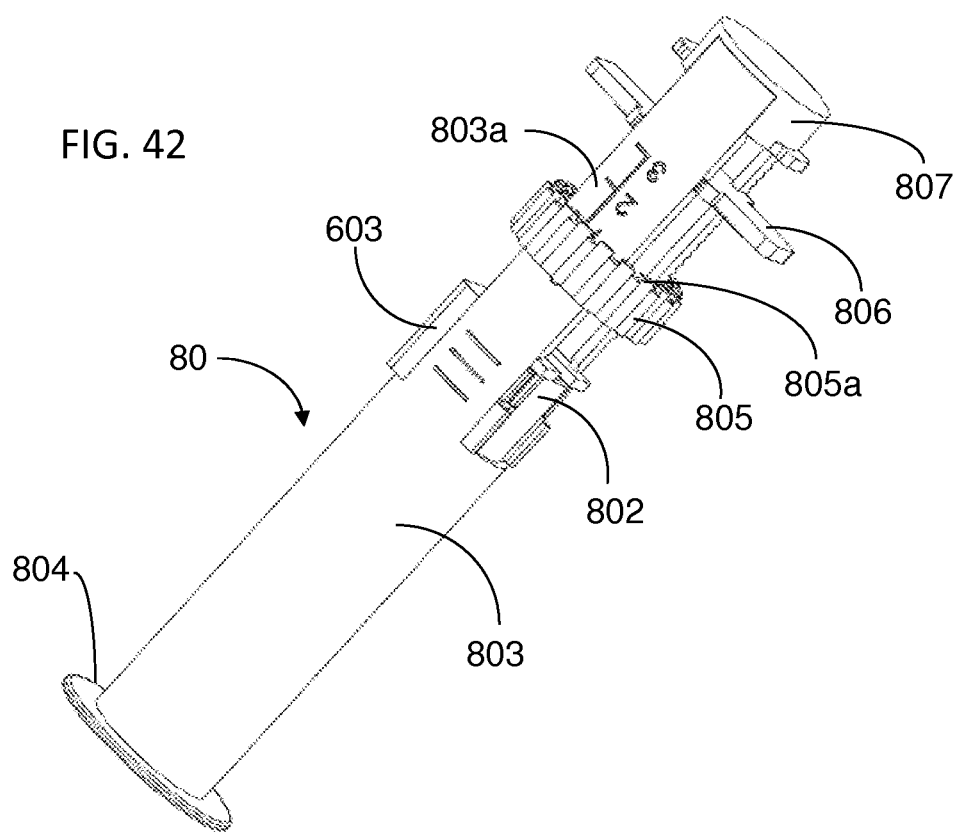
FIGS. 42 and 43 show perspective views of the seventh alternative automatic medication delivery device assembly, before and after injection, according to the invention.
Figure 43:
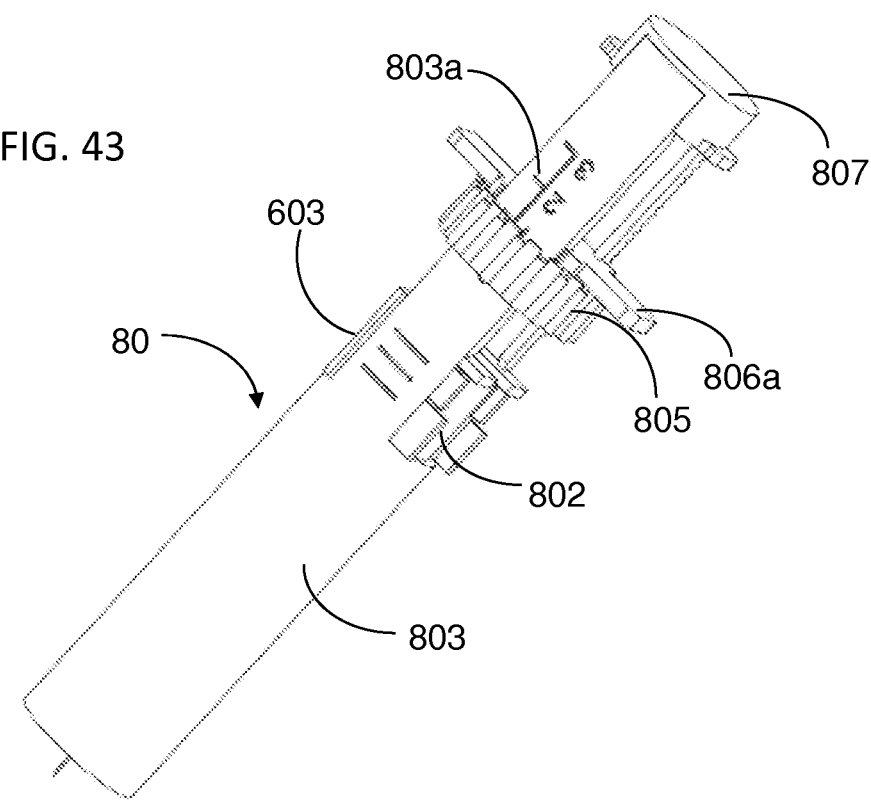
Figure 44:
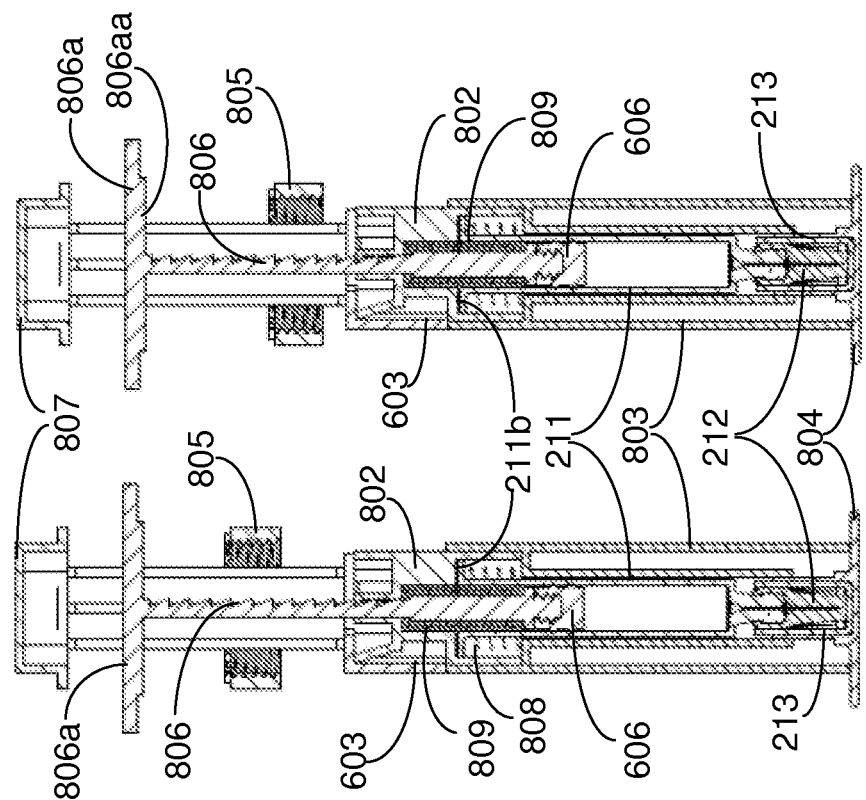
FIG. 44 shows cross-sectional views of the seventh alternative automatic medication delivery device assembly, before and after injection, with different dose settings, according to the invention.
Figure 45:
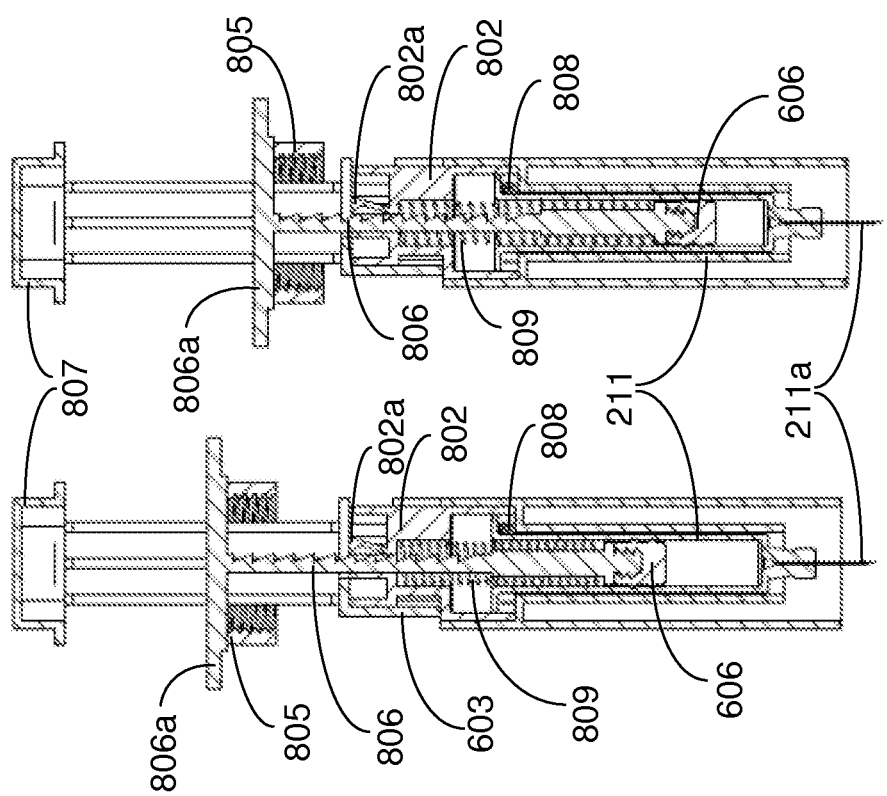
FIG. 45 shows cross-sectional views of the seventh alternative automatic medication delivery device assembly, after injection, with different dose settings, according to the invention.

FIGS. 42-45 illustrate the construction and function mechanism of the seventh alternative automatic medication delivery device assembly 80 according to the invention. The activation mechanism of the automatic medication delivery device 80 is the same as those of the automatic medication delivery device 60. In this automatic medication delivery device assembly 80, the pre-filled syringe 211 is used as medication container. A housing 803 is used to host the pre-filled syringe 211. A cap 807 is placed at the proximal end of the housing 803. A dose setting ring 805 is introduced to set the different injection dose. As shown in FIG. 42, before injection, user moves the dose setting ring 805 along the dose setting area 803a on the housing 803. A needle shield puller 804 is used to remove the needle shield 212 and the needle shield shell 213 before injection. As shown in FIG. 43-45, during injection, user pushes the push button 603 inward. The lock mechanism between the push rod 806 and a connector 802 is released. A driving spring 809 drives the push rod 806 move toward the distal end of the automatic medication delivery device 80. The movement of the push rod 806 stops when the flange feature 806a on the push rod 806 meets the dose setting ring 805. Rib feature 806aa on flange feature 806a engages with teeth feature 805a on the setting ring 805 to prevent further rotational movement of the dose setting ring 805. Different injection doses are achieved by placing the dose setting ring 805 at the different positions. Furthermore, an automatic needle insertion mechanism is introduced for device 80. A driving spring 809 pushes the push rod 806 and the piston 210 and the pre-filled syringe 211 toward the distal end of the automatic medication delivery device 80. A syringe support spring 808 is compressed. A bendable finger feature (hidden in the cross-sectional views), as the same as the one shown in automatic medication delivery device 50, is used to lock the pre-filled syringe 211 in place after the syringe support spring 808 is compressed. Alternatively, design mechanism shown in FIGS. 33-34A can be implemented for the device 80.

Figure 46:
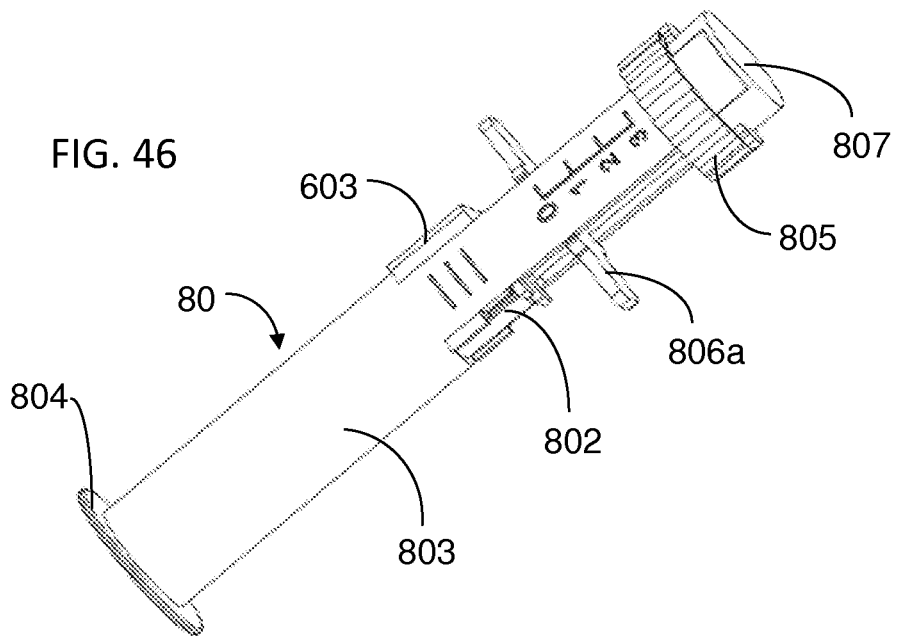
FIG. 46-47 show perspective views of another configuration of the seventh alternative automatic medication delivery device assembly according to the invention.
Figure 47:
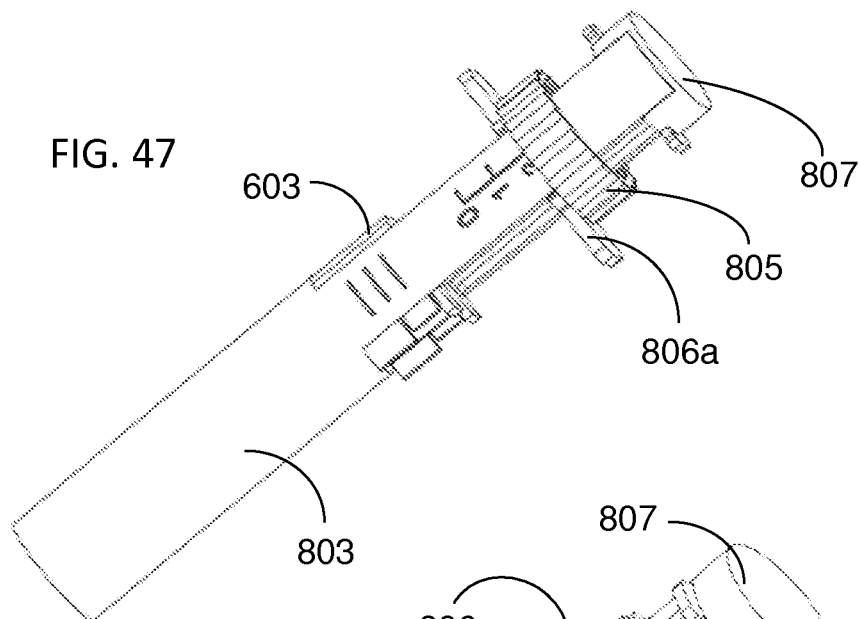

FIGS. 46 and 47 illustrate an alternative configuration of the seventh alternative automatic medication delivery device assembly 80 according to the invention. In this alternative configuration, the dose setting ring 805 is place more proximally than the flange feature 806a on the push rod 806. In this way, the dose setting ring 805 is used to pre-set the maximum dose of injection.

Figure 48:
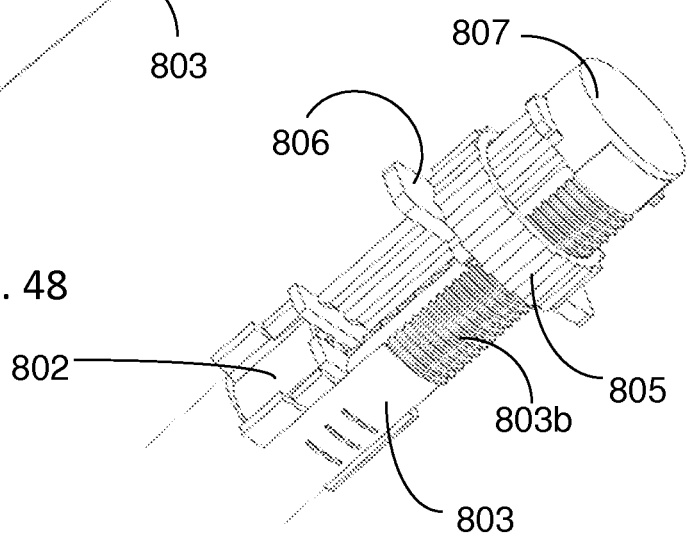
FIG. 48 shows engagements between components of the seventh alternative automatic medication delivery device assembly according to the invention.

FIG. 48 illustrates that the dose setting ring 805 engages with the housing 803 through thread feature 803b on the housing 803.

Figure 49:
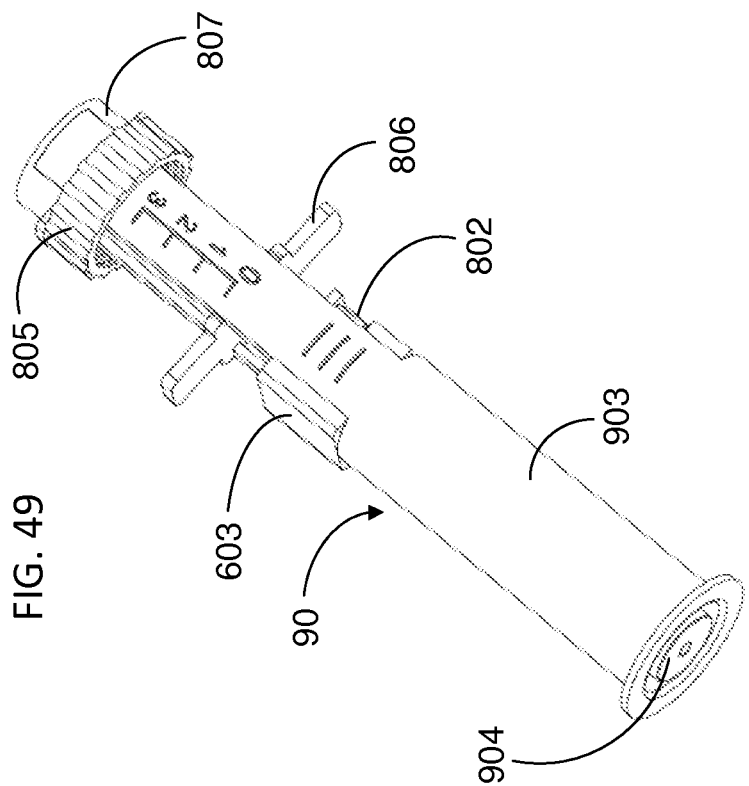
FIG. 49 shows perspective view of the eighth alternative automatic medication delivery device assembly according to the invention.
Figure 50:
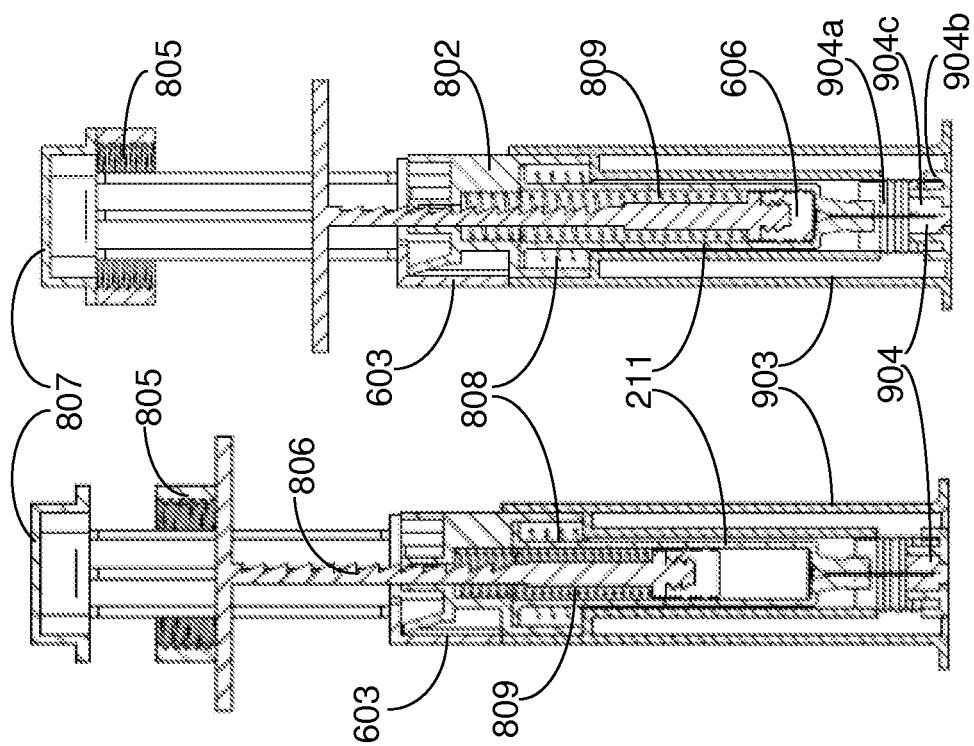
FIG. 50 shows cross-sectional views of the eighth alternative automatic medication delivery device assembly according to the invention.
Figure 51:
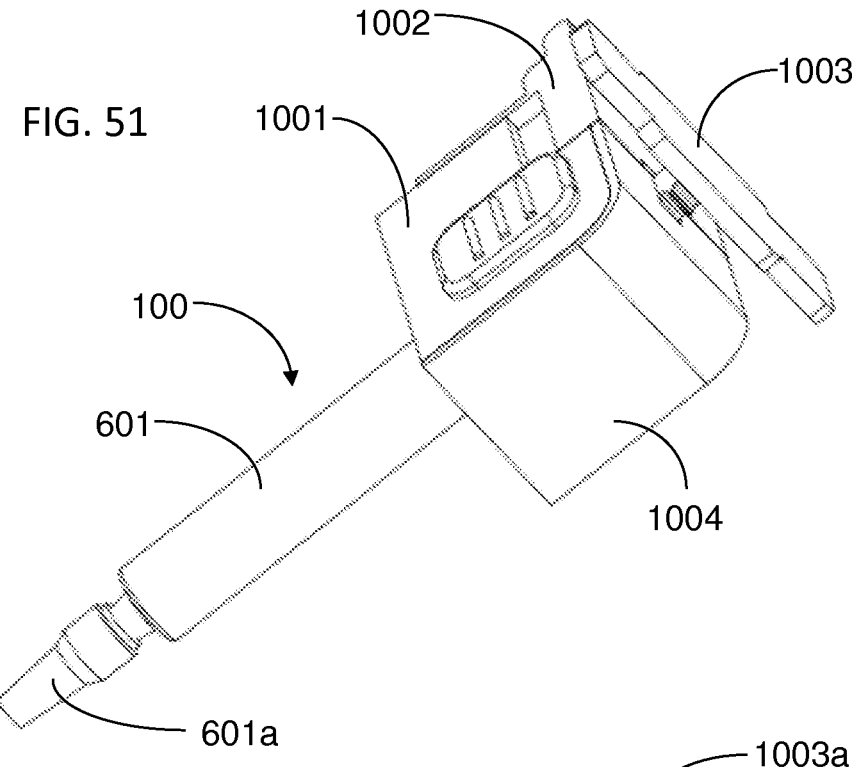
FIGS. 51 and 52 show perspective views of the ninth alternative automatic medication delivery device assembly according to the invention.
Figure 52:
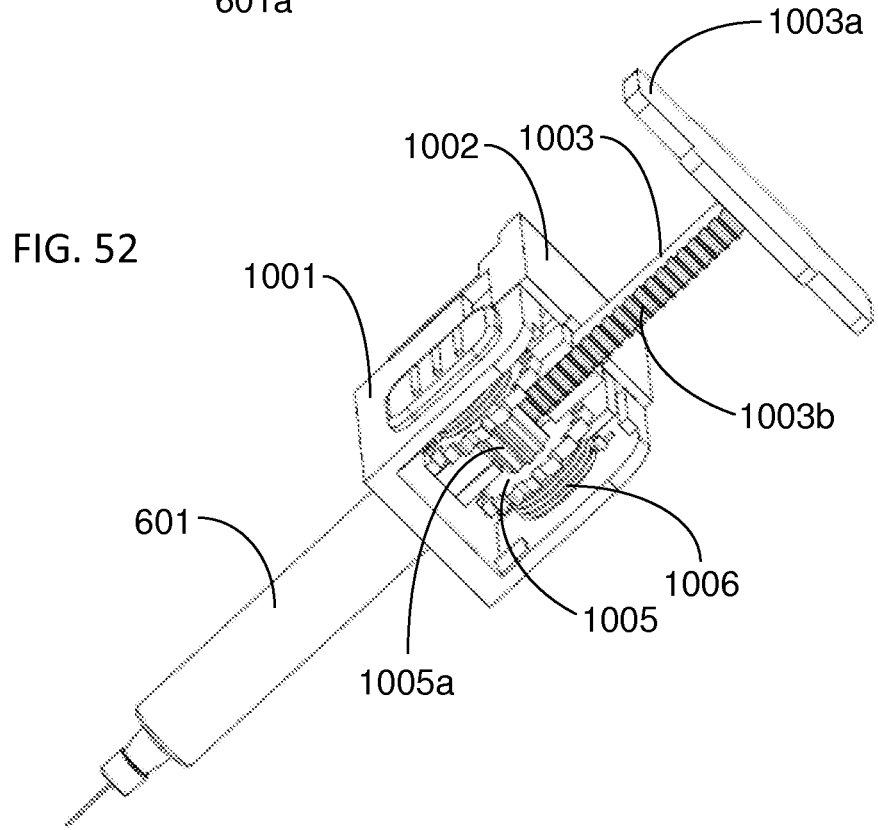

FIGS. 49 and 50 illustrates the construction and function mechanism of the eighth alternative automatic medication delivery device assembly 90 according to the invention. The dose setting mechanism and activation mechanism of the automatic medication delivery device 90 is the same as those of the automatic medication delivery device 80. In this automatic medication delivery device 90, instead of the needle shield 212 and the needle shield shell 213, a compressible needle shield sub-assembly 904 is used. A housing 903 is introduced to host the compressible needle shield sub-assembly 904. The compressible needle shield sub-assembly 904 is formed by a compressible component 904a, a rigid needle shield frame 904b and an elastomeric needle shield 904c. During injection, the automatic medication delivery device assembly 90 is pushed against patient's skin at the injection site. The compressible component 904a collapses. The needle 211a pierces the elastomeric needle shield 904c and is inserted into skin for injection. This design allows user to skip the mannual needle shield removal step before injection. This design also allows pre-set vacuum inside the syringe barrel 211.

Figure 53:
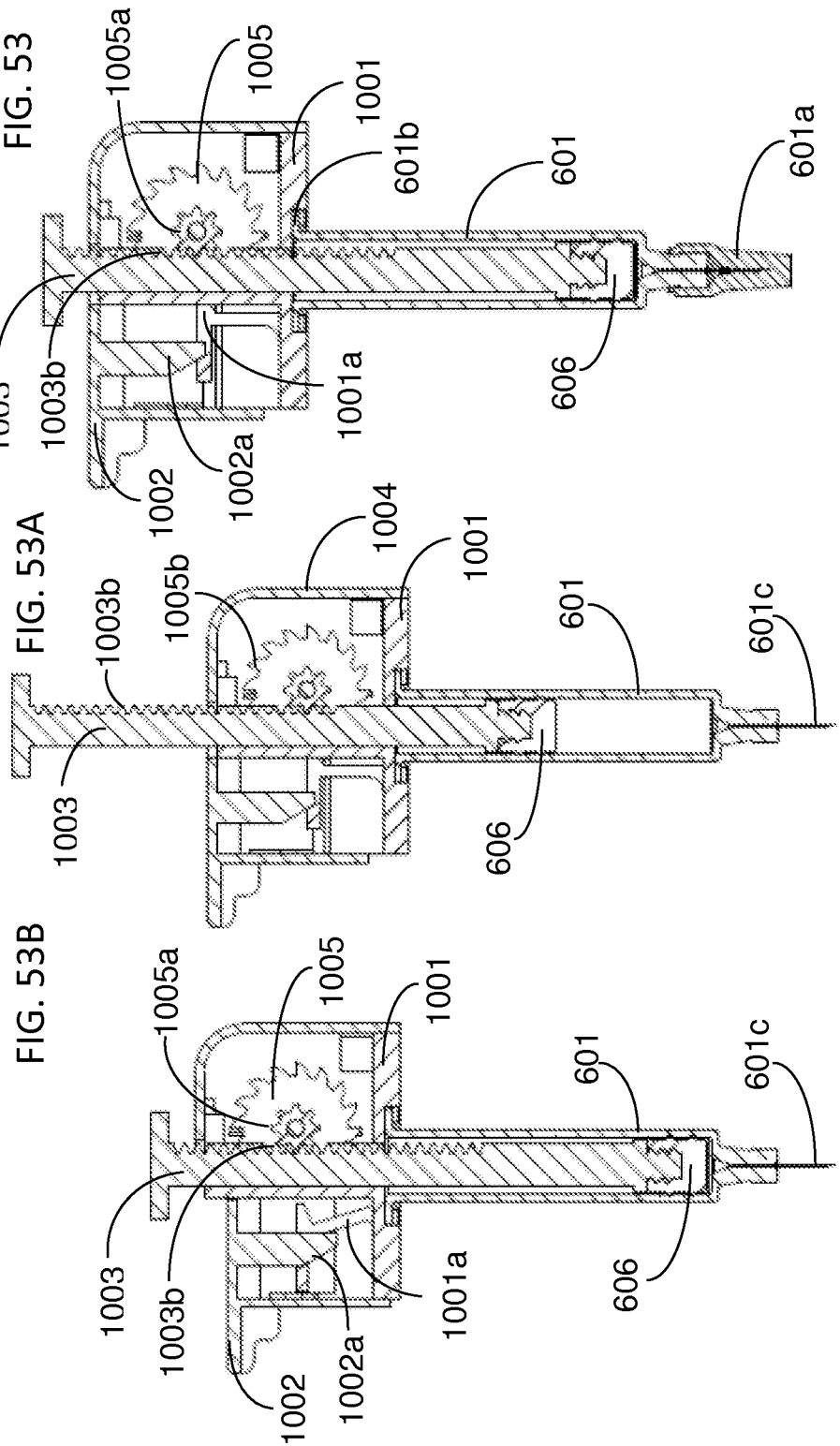
Figure 54:
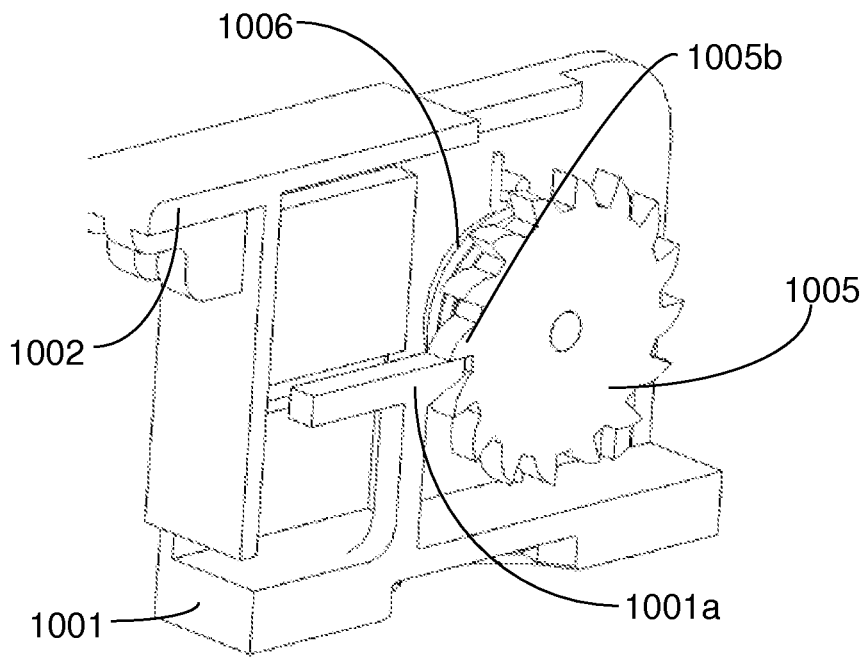
FIGS. 54 and 55 show engagements between components of the ninth alternative automatic medication delivery device assembly according to the invention.
Figure 55:
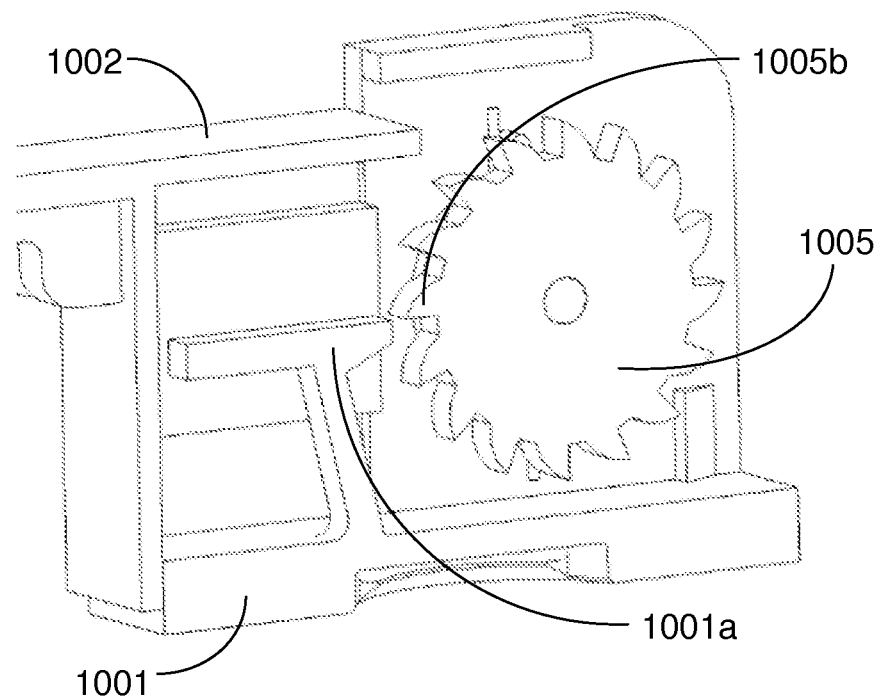

FIGS. 51-55 illustrate the construction and function mechanism of the ninth alternative automatic medication delivery device assembly 100 according to the invention. In this exemplary automatic medication delivery device assembly 100, a syringe 601, as medication container, can be made of either glass or plastic materials. A push button 1002 is used to activate an automatic injection. The push button 1002 is engaged with a connector 1001. The connector 1001 is covered by a cover component 1004. With reference to FIG. 53-53B, user first removes the needle shield 601a. Then, user pulls the flange feature 1003a on a push rod 1003 toward to proximal end of the automatic medication delivery device 100 and draws medication into the syringe 601. When the push rod 1003 is pulled toward to the proximal end of the automatic medication delivery device 100, the teeth feature 1003b engages with the gear feature 1005a on the driving gear 1005 and causes the rotation of the driving gear 1005. The rotation of the driving gear 1005 generates tension torque on a torsion spring 1006. With reference to FIGS. 53 to 53B, the connector 1001 is assembled with syringe 601 through a flange feature 601b on the syringe 601. Before injection, the torsion spring 1006 (hidden in FIGS. 51 to 51B) is in relaxed stage and a piston 606 is located at the distal end of the automatic medication delivery device 100. When drawing medication into the syringe 601, the piston 606 is moved toward to the proximal end of the automatic medication delivery device 100 accordingly. Meantime, the torsion spring 1006 is wound up. The blocking feature 1001a on the connector 1001 engages with a ratchet feature 1005b on the driving gear 1005 in order to block the movement of the push rod 1003 toward the distal end of the automatic medication delivery device 100, driven by the torsion spring 1006. The teeth feature 1003*a* on the push rod 1003 is used to set different injection doses. During injection, the push button 1002 is pushed toward to the distal end of the automatic medication delivery device 100. Through a chamfer feature 1002*a* on the push button 1002, the blocking feature 1001*a* on the connector 1001 is pushed away from the ratchet feature 1005*b* on the driving gear accordingly, and the push rod 1003 is released. The engagement details between blocking feature 1001*a* and the ratchet feature 1005*b* are shown in FIGS. 54 and 55. When the push rod 1003 is released and the torsion spring 1006, through the driving gear 1005, drives the the push rod 1003 to move toward the distal end of the device 100. The piston 606 is pushed downward. Consequently, liquid medication in the syringe 601 is injected into patient's body.

Figures 56, 57:
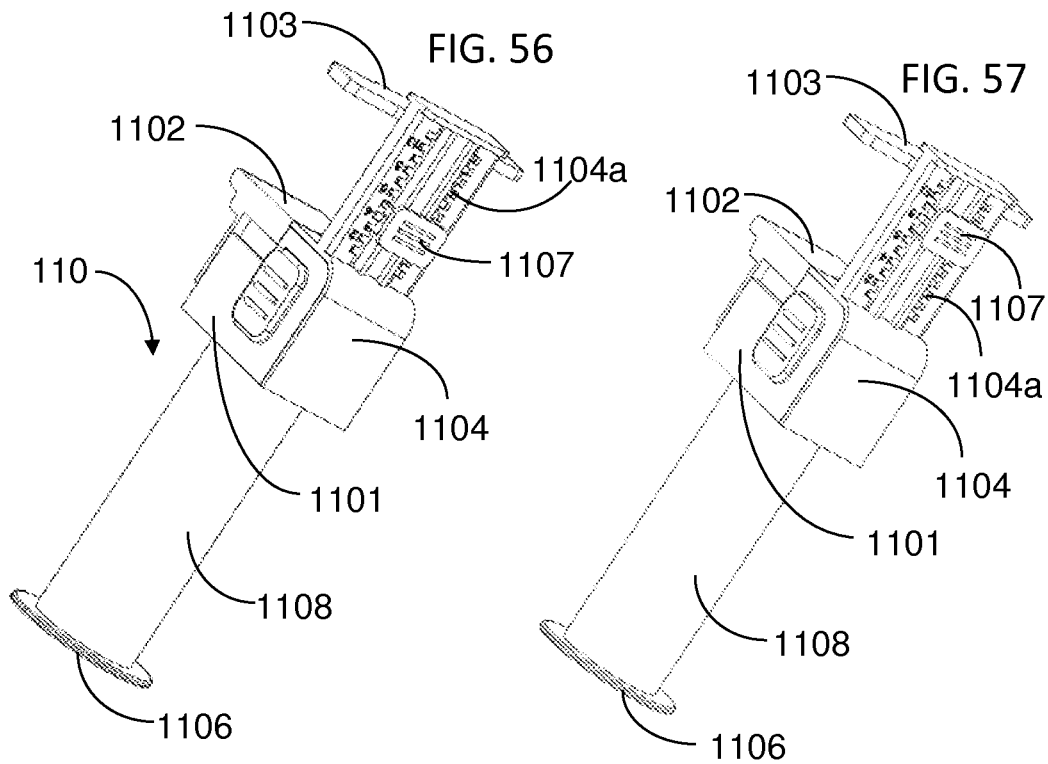
FIGS. 56 and 57 show perspective views of the tenth alternative automatic medication delivery device assembly with different dose settings according to the invention.
Figure 58:
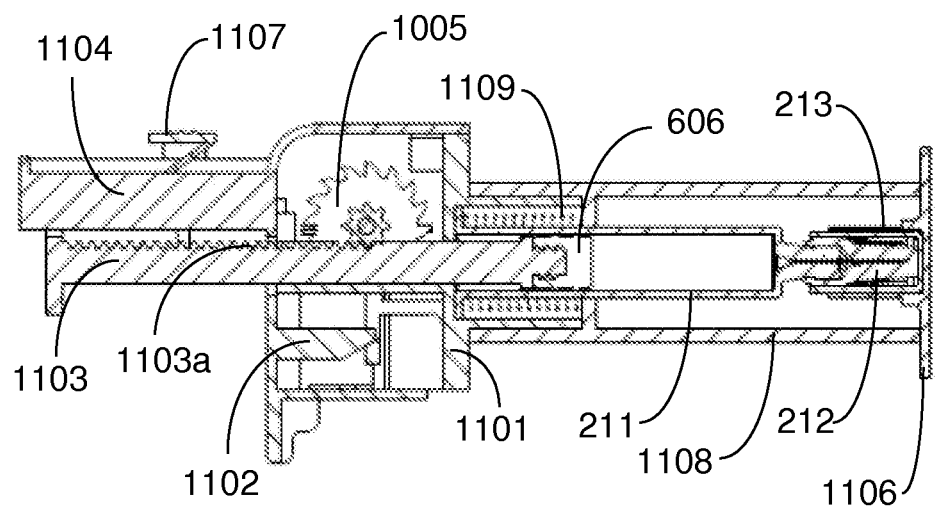
FIG. 58 shows cross-sectional view of the tenth alternative automatic medication delivery device assembly according to the invention.
Figure 59:
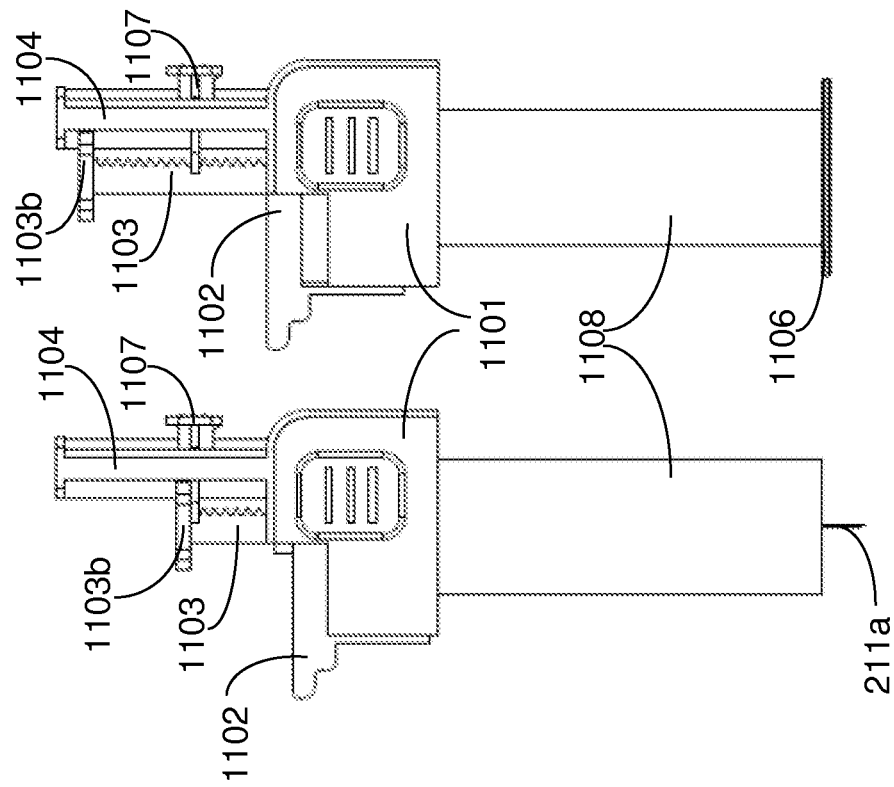
FIG. 59 shows front views of the tenth alternative automatic medication delivery device assembly, before and after injection, according to the invention.

FIGS. 56-59 illustrate the construction and function mechanism of the tenth alternative automatic medication delivery device assembly 110 according to the invention. The activation mechanism of the automatic medication delivery device 110 is the same as those of the automatic medication delivery device 100. In this automatic medication delivery device assembly 110, the pre-filled syringe 211 is used as medication container. A housing 1108 is used to host the pre-filled syringe 211. A cover 1104 is assembled with a connector 1101. A dose setting tab 1107 is introduced to set the different injection dose. Before injection, user moves the dose setting tab 1107 along the dose setting area 1104*a* on the cover 1104. FIGS. 56 and 57 show that the dose setting tap 1107 is placed at different location for different injection doses. A needle shield puller 1106 is used to remove the needle shield 212 and the needle shield shell 213 before injection. During injection, user pushes the push button 1002 to activate the automatic medication delivery device 110. The lock mechanism between a push rod 1103 and the connector 1101 is released. The torsion spring 1006 (hidden) drives the driving gear 1005 to rotate. The rotation of the driving gear 1005 causes the push rod 1103 move toward to the distal end of the automatic medication delivery device 110, through the teeth feature 1103*a* on the push rod 1103. The movement of the push rod 1103 stops when the flange feature 1103*b* on the push rod 1103 meets the dose setting tab 1007 (shown in FIG. 59). Different injection doses are achieved by placing the dose setting tab 1107 at the different positions. Furthermore, an automatic needle insertion mechanism is introduced. The torsion spring 1006 pushes the push rod 1103 and the piston 210 and the pre-filled syringe 211 toward the distal end of the automatic medication delivery device 110. A syringe support spring 1109 is compressed. A bendable finger feature (hidden in the cross-sectional views), as the same as the one shown in automatic medication delivery device 50, is used to lock the pre-filled syringe 211 in place after the syringe support spring 1109 is compressed. Alternatively, design mechanism shown in FIGS. 33-34A can be implemented for the device 80.

Figure 60:
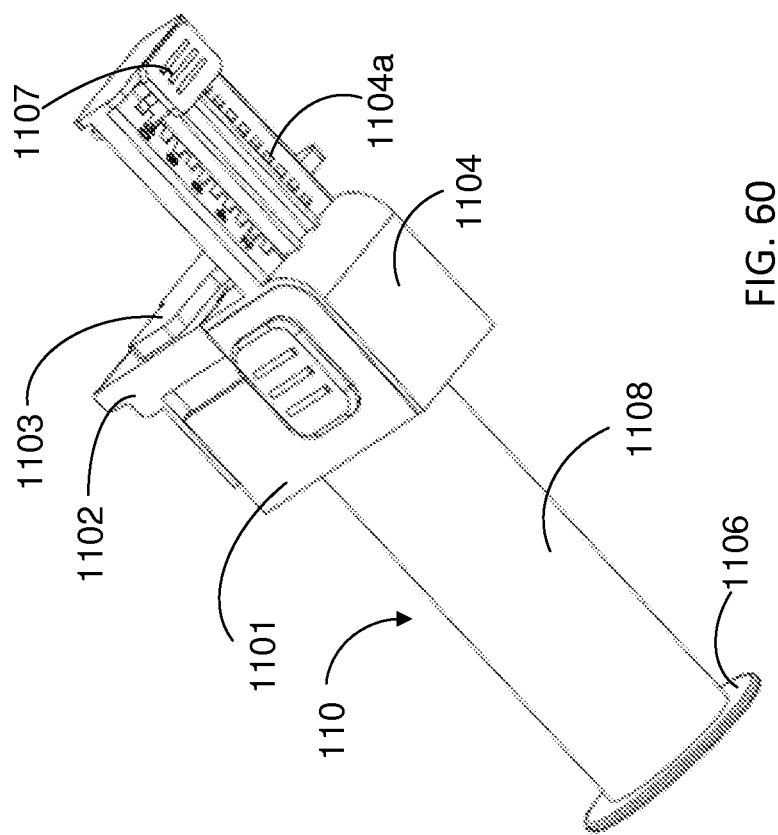
FIG. 60 shows perspective view of another configuration of the tenth alternative automatic medication delivery device assembly according to the invention.

FIG. 60 illustrates an alternative configuration of the tenth alternative automatic medication delivery device assembly 110 according to the invention. In this alternative configuration, the dose setting tab 1107 is placed more proximally than the flange feature 1103*b* on the push rod 1103. In this way, the dose setting tab 1107 is used to pre-set the maximum dose of injection.

In the above embodiments, the dose setting is bidirectional for the automatic medication delivery devices 10, 20, 30, 40, 50, 80 and 110.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medication delivery device, for use with a container having a distal end and a needle being placed at said distal end of said container, comprising:
   a push rod which is movable with respect to at least a portion of said container;
   a resilient member generating axial push force configured to bias said push rod to move toward said distal end of said container;
   a releasable restraining means configured to releasably restrain said push rod in a locked state against said biasing of said resilient member, wherein, upon release of said releasable restraining means, said push rod moves under axial push force of said resilient member toward said distal end of said container;
   a means to adjust amount of axial movement of said push rod with respect to said container in order to dispense a predetermined dose of medication out of said container upon release of said releasable restraining means;
   an activation means configured to release said releasable means; and
   a lock engagement means preventing rotational movement of said push rod, with respect to said container, during dispensing said predetermined dose of medication out of said container, wherein said lock engagement means is disabled in order to allow rotational movement of said push rod, with respect to said container, during adjusting said amount of axial movement of said push rod with respect to said container.

2. The medication delivery device as in claim 1, wherein said means to adjust amount of movement of said push rod with respect to said container is bidirectional.

3. The medication delivery device as in claim 1 further comprising a means to prevent said predetermined dose of medication from being changed.

4. The medication delivery device as in claim 1, wherein said means to adjust amount of movement of said push rod with respect to said container is differentiable for different medications.

5. The medication delivery device as in claim 1 further comprising a means to prevent over dosing.

6. The medication delivery device as in claim 1 further comprising an automatic needle insertion means configured to automatically insert said needle into medication injection site.

7. The medication delivery device as in claim 1 further comprising a means to move said container distally.

8. The medication delivery device as in claim 1 further comprising a means to prevent accidental activation of said medication delivery device.

9. The medication delivery device as in claim 1 further comprising a needle shield to cover said needle before injection.

10. The medication delivery device as in claim 9 wherein said needle shield being pierced by said needle during medication injection.

11. The medication delivery device as in claim 1 further comprising a means to at least partially cover said needle after said predetermined dose of medication is delivered.

* * * * *